US012616844B2

(12) United States Patent
Postlewait et al.

(10) Patent No.: US 12,616,844 B2
(45) Date of Patent: May 5, 2026

(54) SUBSTANTIALLY-MEDIAN-BASED DETERMINATION OF LONG-TERM HEART RATES FROM ECG DATA OF WEARABLE CARDIOVERTER DEFIBRILLATOR (WCD) SYSTEM

(71) Applicant: WEST AFFUM HOLDINGS DAC, Dublin (IE)

(72) Inventors: Steven Postlewait, Seattle, WA (US); Joseph Sullivan, Kirkland, WA (US); Gregory T. Kavounas, Bellevue, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 0 days.

(21) Appl. No.: 18/649,767

(22) Filed: Apr. 29, 2024

(65) Prior Publication Data

US 2024/0278027 A1     Aug. 22, 2024

Related U.S. Application Data

(63) Continuation of application No. 18/310,391, filed on May 1, 2023, now Pat. No. 11,969,606, which is a
(Continued)

(51) Int. Cl.
*A61N 1/04*         (2006.01)
*A61B 5/00*         (2006.01)
(Continued)

(52) U.S. Cl.
CPC .......... *A61N 1/3925* (2013.01); *A61B 5/0245* (2013.01); *A61B 5/282* (2021.01);
(Continued)

(58) Field of Classification Search
CPC ....... A61B 5/0245; A61B 5/282; A61B 5/316; A61B 5/333; A61B 5/352; A61B 5/6805;
(Continued)

(56) References Cited

U.S. PATENT DOCUMENTS 3,724,355 A     4/1973  Busch et al.
3,724,455 A     4/1973  Unger
(Continued)

FOREIGN PATENT DOCUMENTS

DE     102005060985 A1     6/2007
EP         2305110 A1     4/2011
(Continued)

OTHER PUBLICATIONS

Klein, H. U., et al., Risk Stratification for Implantable Cardioverter Defibrillator therapy: The Role of the Wearable Cardioverter-Defibrillator, Clinical update, European Heart Journal, May 31, 2013, pp. 1-14, doi:10.1093/eurheartj/eht167, European Society of Cardiology.
(Continued)

*Primary Examiner* — Carl H Layno
*Assistant Examiner* — Anh-Khoa N Dinh
(74) *Attorney, Agent, or Firm* — Seed Intellectual Property Law Group LLP

(57)         ABSTRACT

A wearable medical monitoring (WMM) system may be worn for a long time. Some embodiments of WMM systems are wearable cardioverter defibrillator (WCD) systems. In such systems, ECG electrodes sense an ECG signal of the patient, and store it over the long-term. The stored ECG signal can be analyzed for helping long-term heart rate monitoring of the patient. The heart rate monitoring can be assisted a) by special filtering techniques that remove short-term variations inherent in patients' short-term heart rate determinations, and b) by indication techniques that indicate
(Continued)

SAMPLE COMPONENTS OF WEARABLE
CARDIOVERTER DEFIBRILLATOR (WCD) SYSTEM
WORN OVER TIME when conditions hampered sensing of the ECG signal too much for a reliable heart rate determination.

18 Claims, 18 Drawing Sheets

Related U.S. Application Data continuation of application No. 17/317,157, filed on May 11, 2021, now Pat. No. 11,666,769, which is a continuation of application No. 16/380,037, filed on Apr. 10, 2019, now Pat. No. 11,000,691.

(60) Provisional application No. 62/662,128, filed on Apr. 24, 2018.

(51) Int. Cl.

| | |
|---|---|
| A61B 5/0245 | (2006.01) |
| A61B 5/282 | (2021.01) |
| A61B 5/316 | (2021.01) |
| A61B 5/333 | (2021.01) |
| A61B 5/352 | (2021.01) |
| A61N 1/39 | (2006.01) |

(52) U.S. Cl.
CPC .............. *A61B 5/316* (2021.01); *A61B 5/333* (2021.01); *A61B 5/352* (2021.01); *A61B 5/6805* (2013.01); *A61B 5/7221* (2013.01); *A61B 5/742* (2013.01); *A61N 1/046* (2013.01); *A61N 1/0484* (2013.01); *A61N 1/3904* (2017.08)

(58) Field of Classification Search
CPC ..... A61B 5/7221; A61B 5/742; A61B 5/0006; A61B 5/4836; A61B 5/363; A61B 5/361; A61B 5/35; A61B 5/6823; A61B 5/6804; A61B 5/0205; A61B 5/053; A61B 5/0538; A61B 5/086; A61B 5/103; A61B 5/1116; A61B 5/4878; A61B 5/6846; A61B 5/686; A61B 5/7264; A61B 5/7285; A61N 1/046; A61N 1/0484; A61N 1/3904; A61N 1/3925; A61N 1/3987; A61N 1/37282; A61N 1/3993; A61N 1/39044; A61N 1/0476; A61N 1/37211; A61N 1/37264; A61N 1/3625; A61N 1/3937; A61N 1/08; A61N 1/37247; A61N 1/3968; A61N 1/025; A61N 1/3621; A61N 1/36542; A61N 1/365; A61N 1/37258; A61N 1/3655; A61N 2001/083; A61N 1/36521; A61N 1/36585; A61N 1/3702; G16H 50/20
See application file for complete search history.

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bomn et al. |
| 5,353,793 A | 10/1994 | Bomn |
| RE34,800 E | 11/1994 | Hutchins |
| 5,394,892 A | 3/1995 | Kenny |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 8/2002 | Brack et al. |
| 6,450,942 B1 | 9/2002 | Lapanashvili et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,099,715 B2 | 8/2006 | Korzinov et al. |
| 7,212,850 B2 | 5/2007 | Prystowsky et al. |
| 7,559,902 B2 | 7/2009 | Ting et al. |
| 7,587,237 B2 | 9/2009 | Korzinov et al. |
| 7,753,759 B2 | 7/2010 | Pintor et al. |
| 7,865,238 B2 | 1/2011 | Brink |
| 7,870,761 B2 | 1/2011 | Valentine et al. |
| 7,907,996 B2 | 3/2011 | Prystowsky et al. |
| 7,941,207 B2 | 5/2011 | Korzinov |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,375,151 B1 | 6/2016 | Hopenfeld et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,724,008 B2 | 8/2017 | Sullivan et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |

(56)                    References Cited

U.S. PATENT DOCUMENTS

| | | | |
|---|---|---|---|
| 10,192,387 B2 | 1/2019 | Brinig et al. | |
| 10,307,133 B2 | 6/2019 | Kaib | |
| 10,463,867 B2 | 11/2019 | Kaib et al. | |
| 10,589,110 B2 | 3/2020 | Oskin et al. | |
| 10,599,814 B2 | 3/2020 | Landrum et al. | |
| 11,000,691 B2 * | 5/2021 | Postlewait | A61B 5/6805 |
| 11,666,769 B2 * | 6/2023 | Postlewait | A61B 5/282 600/509 |
| 11,969,606 B2 * | 4/2024 | Postlewait | A61B 5/333 |
| 2002/0181680 A1 | 12/2002 | Linder et al. | |
| 2003/0023178 A1 * | 1/2003 | Bischoff | A61B 5/681 600/515 |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2006/0173499 A1 | 8/2006 | Hampton et al. | |
| 2006/0247549 A1 * | 11/2006 | Chan | A61B 5/0006 600/519 |
| 2008/0312709 A1 | 12/2008 | Volpe et al. | |
| 2009/0005827 A1 | 1/2009 | Weintraub et al. | |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0191476 A1 | 7/2012 | Reid et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0144355 A1 | 6/2013 | Macho et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0046391 A1 * | 2/2014 | Cowan | H04W 4/90 607/5 |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0161554 A1 | 6/2015 | Sweeney et al. | |
| 2015/0297135 A1 | 10/2015 | Shoshani et al. | |
| 2015/0328472 A1 | 11/2015 | Sullivan et al. | |
| 2016/0004831 A1 | 1/2016 | Carlson et al. | |
| 2016/0067514 A1 * | 3/2016 | Sullivan | A61N 1/3987 607/6 |
| 2016/0076175 A1 | 3/2016 | Rock et al. | |
| 2016/0076176 A1 | 3/2016 | Rock et al. | |
| 2016/0082277 A1 | 3/2016 | Foshee et al. | |
| 2016/0113581 A1 | 4/2016 | Amir et al. | |
| 2016/0256104 A1 | 9/2016 | Romem et al. | |
| 2016/0283900 A1 | 9/2016 | Johnson et al. | |
| 2016/0342761 A1 * | 11/2016 | Whiting | G16H 10/60 |
| 2017/0014073 A1 | 1/2017 | Shoshani et al. | |
| 2017/0027469 A1 | 2/2017 | Amir et al. | |
| 2017/0036066 A1 | 2/2017 | Chahine | |
| 2017/0040758 A1 | 2/2017 | Amir et al. | |
| 2017/0162840 A1 | 6/2017 | Pendry | |
| 2017/0319862 A1 | 11/2017 | Foshee, Jr. et al. | |
| 2017/0367591 A1 | 12/2017 | Jorgensen | |
| 2018/0116537 A1 | 5/2018 | Sullivan et al. | |
| 2018/0117299 A1 | 5/2018 | Gustavson et al. | |
| 2018/0184933 A1 | 7/2018 | Sullivan et al. | |
| 2018/0185662 A1 | 7/2018 | Foshee, Jr. et al. | |
| 2018/0243578 A1 | 8/2018 | Volosin | |
| 2018/0318593 A1 | 11/2018 | Sullivan | |
| 2018/0361165 A1 | 12/2018 | Jaax et al. | |
| 2019/0030352 A1 | 1/2019 | Sullivan et al. | |
| 2019/0076666 A1 | 3/2019 | Medema | |
| 2019/0116896 A1 | 4/2019 | Armour et al. | |
| 2019/0321650 A1 | 10/2019 | Raymond et al. | |

FOREIGN PATENT DOCUMENTS

| | | |
|---|---|---|
| EP | 3380189 B1 | 10/2018 |
| JP | 4320257 B2 | 8/2009 |
| JP | 2014526282 A | 10/2014 |
| JP | 5963767 B2 | 8/2016 |
| WO | 1998039061 A2 | 9/1998 |
| WO | 2011/146448 A1 | 11/2011 |
| WO | 2012064604 A1 | 5/2012 |
| WO | 2012/151160 A1 | 11/2012 |
| WO | 2015/056262 A1 | 4/2015 |
| WO | 2016/077786 A1 | 5/2016 |

OTHER PUBLICATIONS

LIECOR LifeVest System Model WCD 3100 Operator's Manual, 2006 PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Metting, et al., High-Quality Recording of Bioelectric Events Part 1: Interference Reduction, Theory and Practice, Review, Medical & Biological Engineering & Computing, Sep. 1990, pp. 389-397, IFMBE.

Pagan-Carlo, et al., "Encircling Overlapping Multipulse Shock Waveforms for Transthoracic Defibrillation," JACC Journals, Dec. 1998, vol. 32 Issue 7, pp. 2065-2071.

Zoll, LifeVest, Proven protection from Sudden Cardiac Death, 2017, Pittsburgh PA, USA, 4 pages.

International Search Report and Written Opinion for PCT Application No. PCT/US2015/051726, dated May 20, 2016, European Patent Office, Rijswijk, (11 pages).

* cited by examiner

SAMPLE COMPONENTS OF WEARABLE
CARDIOVERTER DEFIBRILLATOR (WCD) SYSTEM
WORN OVER TIME

SAMPLE COMPONENTS OF EXTERNAL DEFIBRILLATOR

COMPONENTS OF
SAMPLE WCD SYSTEM,
AND DOWNLOAD OF DATA FOR
PROCESSING AND DISPLAY

MULTIPLE ELECTRODES FOR
SENSING ECG SIGNALS ALONG
DIFFERENT VECTORS

577

510
ECG SIGNAL
OVER TIME

520
ANALYZED
ECG SIGNAL
SEGMENTS

530
RAW HR VALUES

540   FIRST
TIME BINS

550 FIRST
HR VALUES

555 FILTER

560 FILTERED
FIRST HR VALUES

570   SECOND
TIME BINS

580 SECOND
HR VALUES

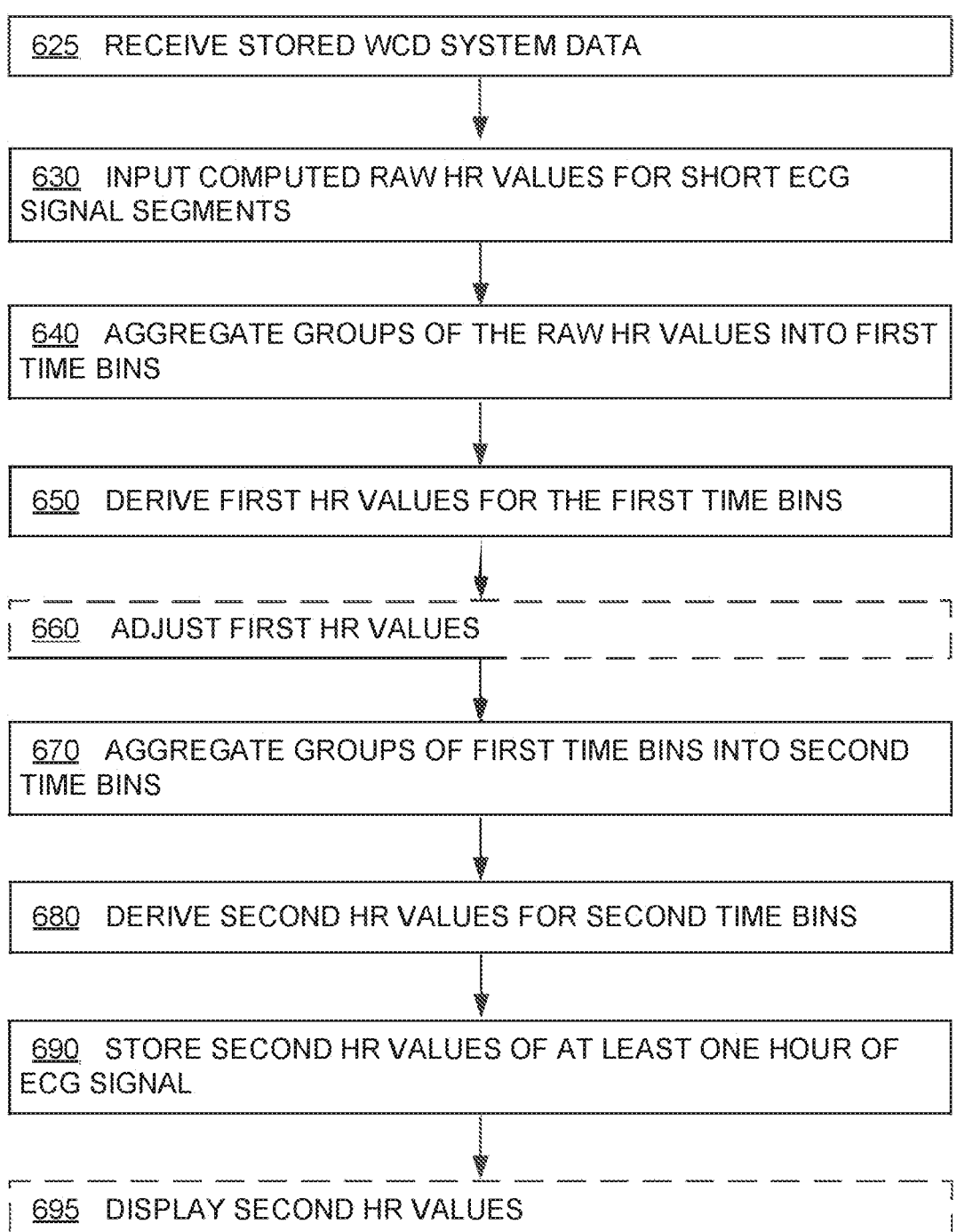

600

625   RECEIVE STORED WCD SYSTEM DATA

630   INPUT COMPUTED RAW HR VALUES FOR SHORT ECG SIGNAL SEGMENTS

640   AGGREGATE GROUPS OF THE RAW HR VALUES INTO FIRST TIME BINS

650   DERIVE FIRST HR VALUES FOR THE FIRST TIME BINS

660   ADJUST FIRST HR VALUES

670   AGGREGATE GROUPS OF FIRST TIME BINS INTO SECOND TIME BINS

680   DERIVE SECOND HR VALUES FOR SECOND TIME BINS

690   STORE SECOND HR VALUES OF AT LEAST ONE HOUR OF ECG SIGNAL

695   DISPLAY SECOND HR VALUES

FIG. 6

_METHODS_

*DETERMINING MIDDLEMOST-RANKED*
*HR VALUES OF SETS*

_SAMPLE FILTERING_
_WITH NO ADJUSTMENT OF VALUE_

SAMPLE FILTERING
WITH ADJUSTMENT OF VALUE

_SAMPLE FILTERING_
_WITH NO ADJUSTMENT OF VALUE_

900

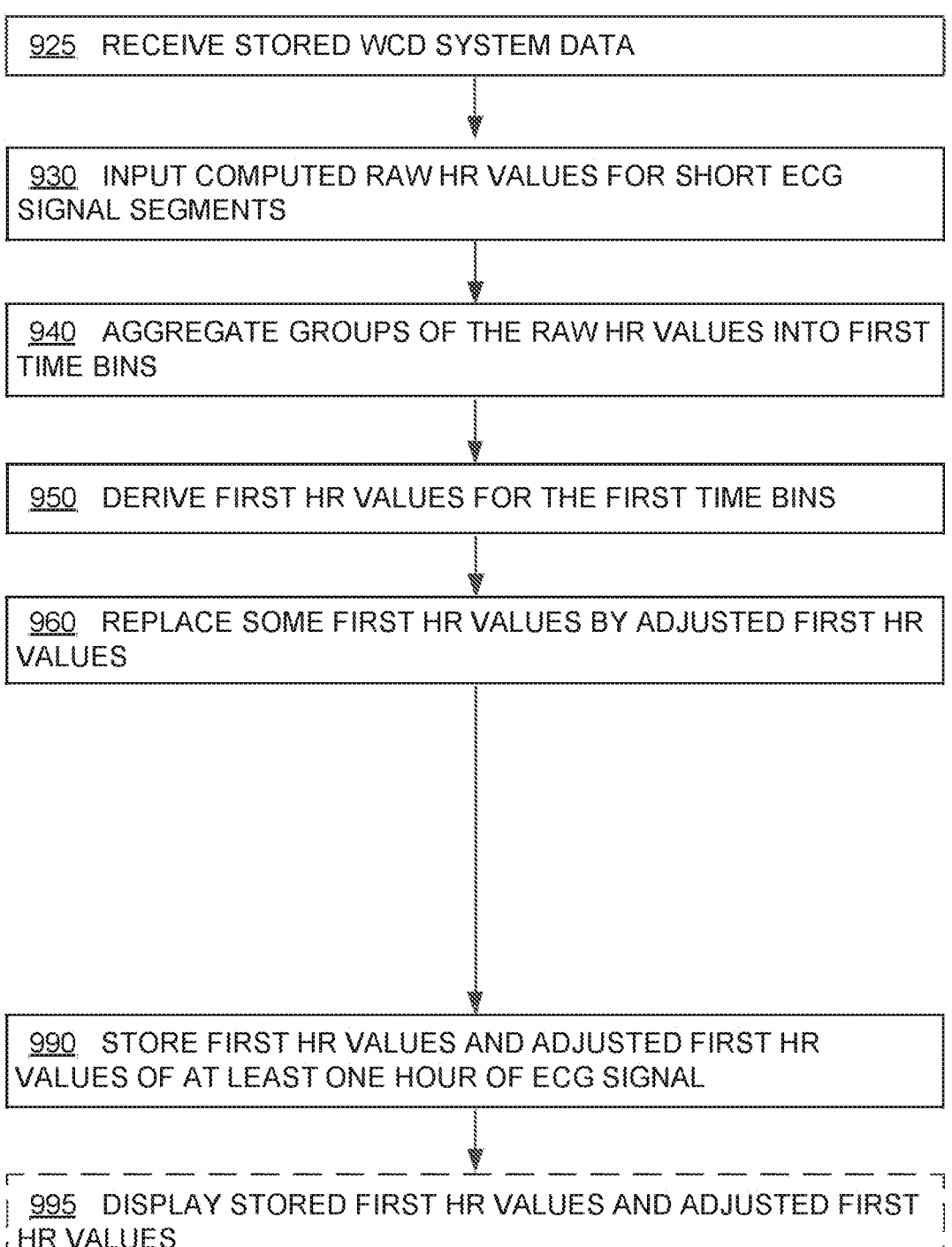

925   RECEIVE STORED WCD SYSTEM DATA

930   INPUT COMPUTED RAW HR VALUES FOR SHORT ECG SIGNAL SEGMENTS

940   AGGREGATE GROUPS OF THE RAW HR VALUES INTO FIRST TIME BINS

950   DERIVE FIRST HR VALUES FOR THE FIRST TIME BINS

960   REPLACE SOME FIRST HR VALUES BY ADJUSTED FIRST HR VALUES

990   STORE FIRST HR VALUES AND ADJUSTED FIRST HR VALUES OF AT LEAST ONE HOUR OF ECG SIGNAL

995   DISPLAY STORED FIRST HR VALUES AND ADJUSTED FIRST HR VALUES

FIG. 9                                    *METHODS*

1100

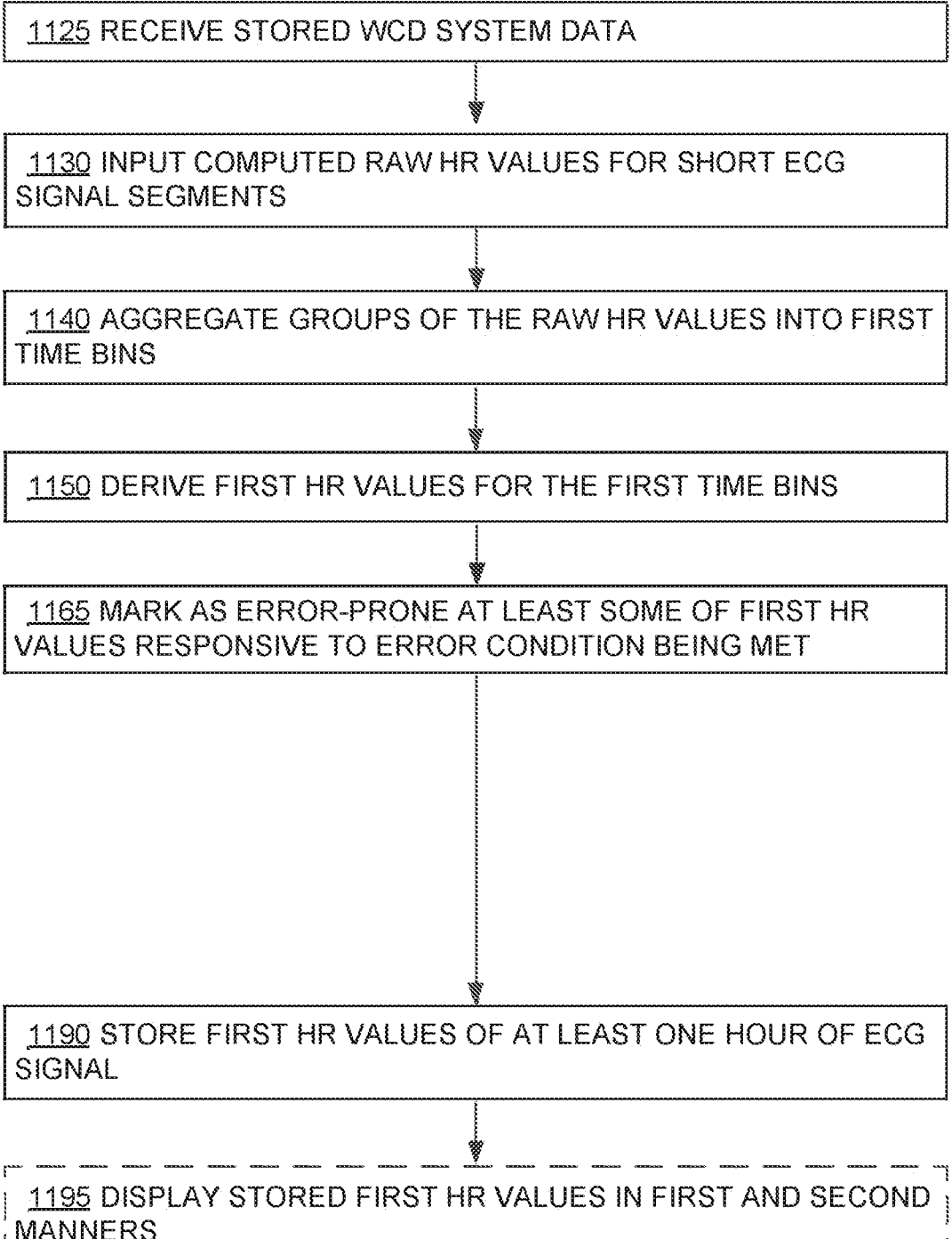

1125 RECEIVE STORED WCD SYSTEM DATA

1130 INPUT COMPUTED RAW HR VALUES FOR SHORT ECG SIGNAL SEGMENTS

1140 AGGREGATE GROUPS OF THE RAW HR VALUES INTO FIRST TIME BINS

1150 DERIVE FIRST HR VALUES FOR THE FIRST TIME BINS

1165 MARK AS ERROR-PRONE AT LEAST SOME OF FIRST HR VALUES RESPONSIVE TO ERROR CONDITION BEING MET

1190 STORE FIRST HR VALUES OF AT LEAST ONE HOUR OF ECG SIGNAL

1195 DISPLAY STORED FIRST HR VALUES IN FIRST AND SECOND MANNERS

FIG. 11                                    METHODS

LONG-TERM HEART RATE
WITH ERROR INDICATIONS

LONG-TERM HEART RATE
WITH NO ERROR INDICATIONS

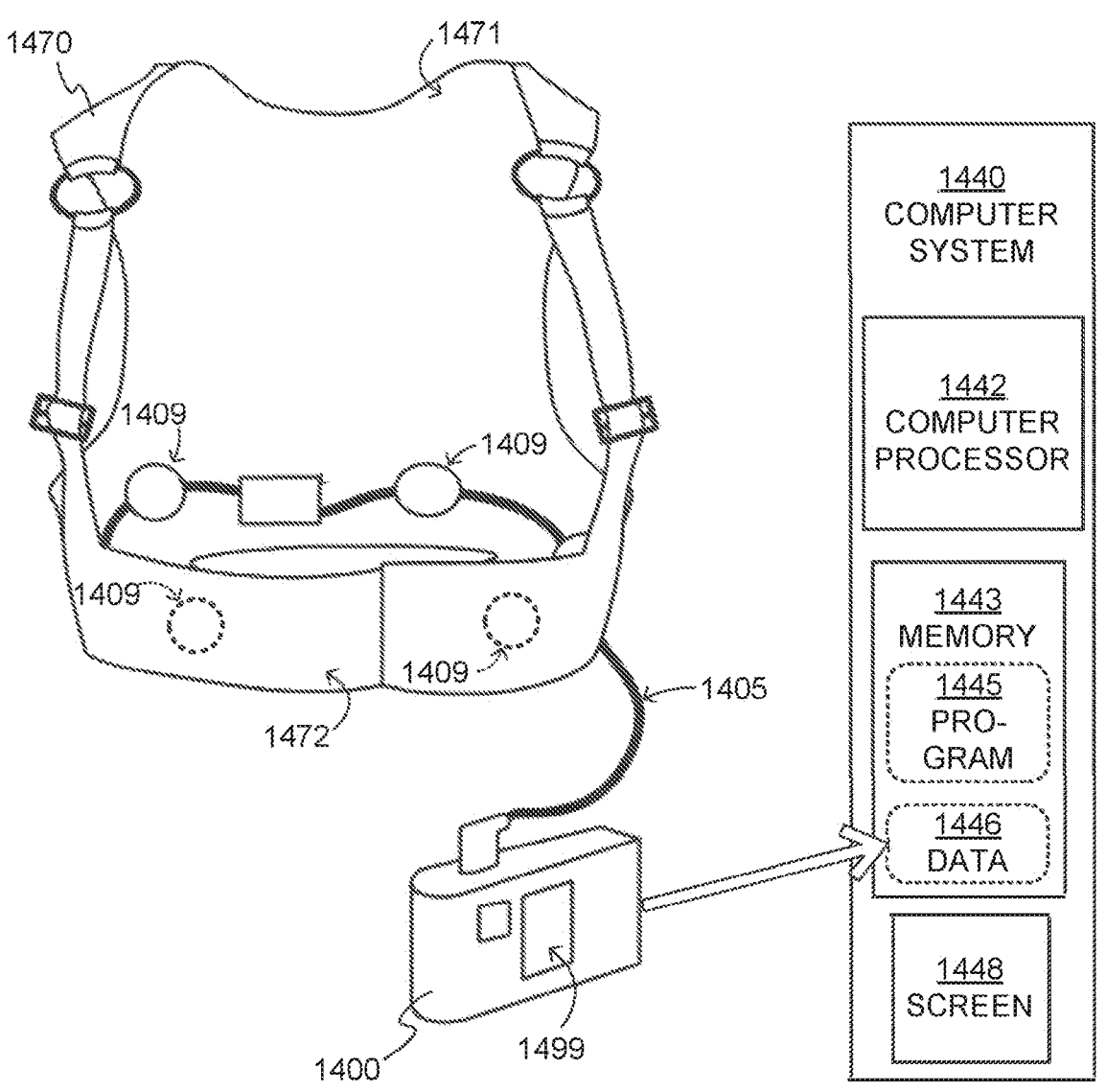
FIG. 14    COMPONENTS OF SAMPLE WMM SYSTEM, AND DOWNLOAD OF DATA FOR PROCESSING AND DISPLAY

1500

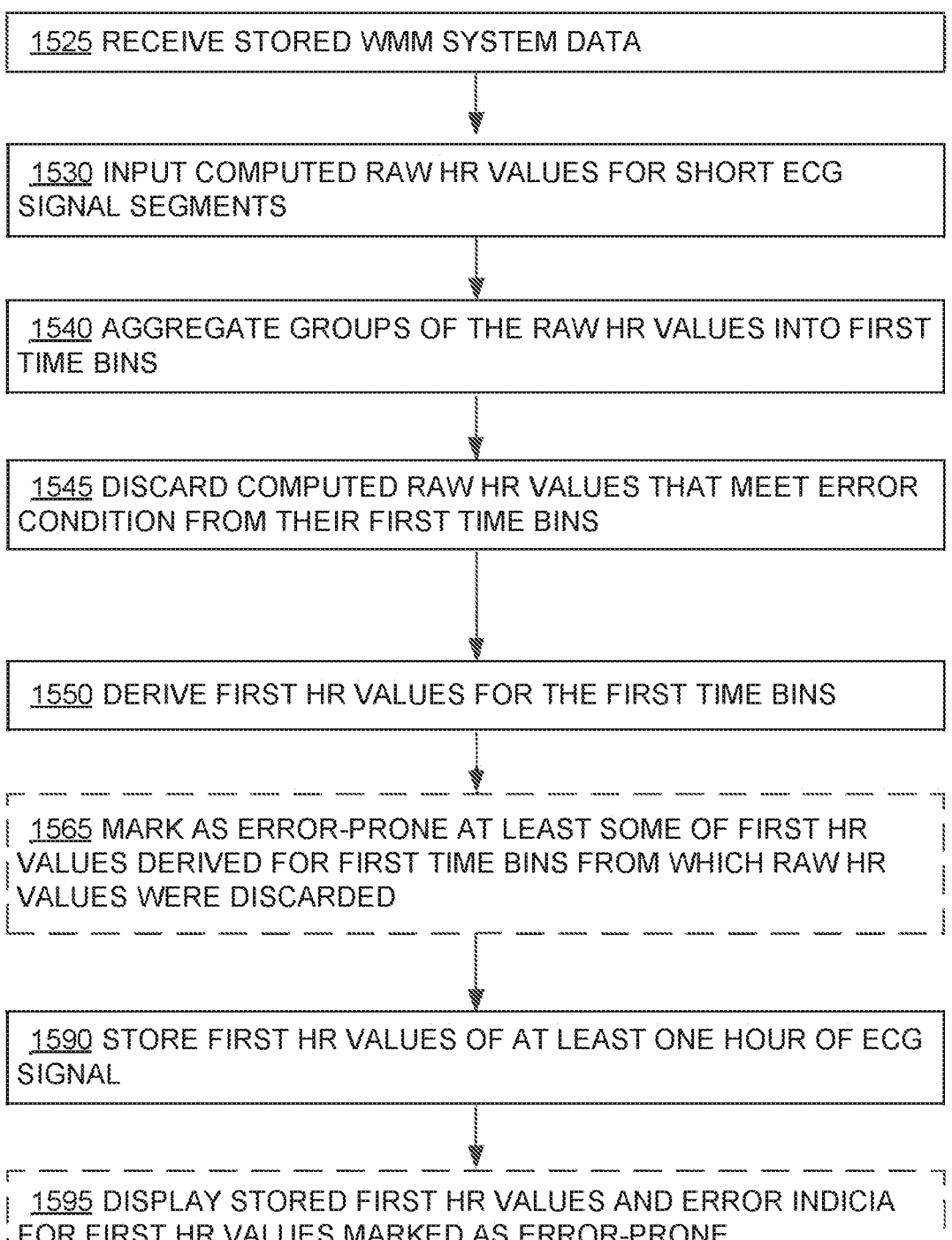

1525 RECEIVE STORED WMM SYSTEM DATA

1530 INPUT COMPUTED RAW HR VALUES FOR SHORT ECG SIGNAL SEGMENTS

1540 AGGREGATE GROUPS OF THE RAW HR VALUES INTO FIRST TIME BINS

1545 DISCARD COMPUTED RAW HR VALUES THAT MEET ERROR CONDITION FROM THEIR FIRST TIME BINS

1550 DERIVE FIRST HR VALUES FOR THE FIRST TIME BINS

1565 MARK AS ERROR-PRONE AT LEAST SOME OF FIRST HR VALUES DERIVED FOR FIRST TIME BINS FROM WHICH RAW HR VALUES WERE DISCARDED

1590 STORE FIRST HR VALUES OF AT LEAST ONE HOUR OF ECG SIGNAL

1595 DISPLAY STORED FIRST HR VALUES AND ERROR INDICIA FOR FIRST HR VALUES MARKED AS ERROR-PRONE

FIG. 15                    METHODS

LONG-TERM HEART RATE
WITH ERROR INDICIA

SUBSTANTIALLY-MEDIAN-BASED DETERMINATION OF LONG-TERM HEART RATES FROM ECG DATA OF WEARABLE CARDIOVERTER DEFIBRILLATOR (WCD) SYSTEM

CROSS REFERENCE TO RELATED PATENT APPLICATIONS

This patent application is a continuation of U.S. application Ser. No. 18/310,391, filed on May 1, 2023, now issued as U.S. Pat. No. 11,969,606, which is a continuation of U.S. application Ser. No. 17/317,157, filed on May 11, 2021, now issued as U.S. Pat. No. 11,666,769, which is a continuation of U.S. Application No. 16/380,037, filed on Apr. 10, 2019, now issued as U.S. Pat. No. 11,000,691, which claims priority from U.S. provisional patent application Ser. No. 62/662,118, filed on Apr. 24, 2018, each of which are incorporated by reference in its entirety.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim. Some observers have thought that SCA is the same as a heart attack, which it is not.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

As a further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear. The WCD system further includes electronic components, such as a defibrillator and electrodes, coupled to the harness, vest, or other garment. When the patient wears the WCD system, the electrodes may make good electrical contact with the patient's skin, and therefore can help sense the patient's ECG. If a shockable heart arrhythmia is detected from the ECG, then the defibrillator delivers an appropriate electric shock through the patient's body, and thus through the heart. This may restart the patient's heart and thus save their life.

All subject matter discussed in this Background section of this document is not necessarily prior art, and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventors. This approach in and of itself may also be inventive.

BRIEF SUMMARY

The present description gives instances of computer systems, storage media that may store programs, and methods for determining a long-term heart rate of a patient, the use of which may help overcome problems and limitations of the prior art.

A wearable medical monitoring (WMM) system may be worn for a long time. Some embodiments of WMM systems are wearable cardioverter defibrillator (WCD) systems. In such systems, ECG electrodes sense an ECG signal of the patient, and store it over the long-term. The stored ECG signal can be analyzed for helping long-term heart rate monitoring of the patient. The heart rate monitoring can be assisted a) by special filtering techniques that remove short-term variations inherent in patients' short-term heart rate determinations, and b) by indication techniques that indicate when conditions hampered sensing of the ECG signal too much for a reliable heart rate determination.

These and other features and advantages of the claimed invention will become more readily apparent in view of the embodiments described and illustrated in this specification, namely in this written specification and the associated drawings.

BRIEF DESCRIPTION OF THE DRAWINGS

FIG. 6 is a flowchart for illustrating sample methods according to embodiments for WCD systems.

FIG. 9 is a flowchart for illustrating sample methods according to embodiments for WCD systems.

FIG. 11 is a flowchart for illustrating sample methods according to embodiments for WCD systems.

FIG. 14 is a diagram of sample embodiments of components of a WMM system, where further WMM stored data is downloaded to a computer system made according to embodiments.

FIG. 15 is a flowchart for illustrating sample methods according to embodiments for WMM systems.

DETAILED DESCRIPTION

As has been mentioned, the present description is about facilitating long-term heart rate monitoring of a patient who is wearing a wearable cardioverter defibrillator (WCD) system. Embodiments are now described in more detail.

A wearable cardioverter defibrillator (WCD) system according to embodiments may protect an ambulatory patient by electrically restarting their heart if needed. Such a WCD system may have a number of components. These components can be provided separately as modules that can be interconnected, or can be combined with other components, and so on.

Figure 1:
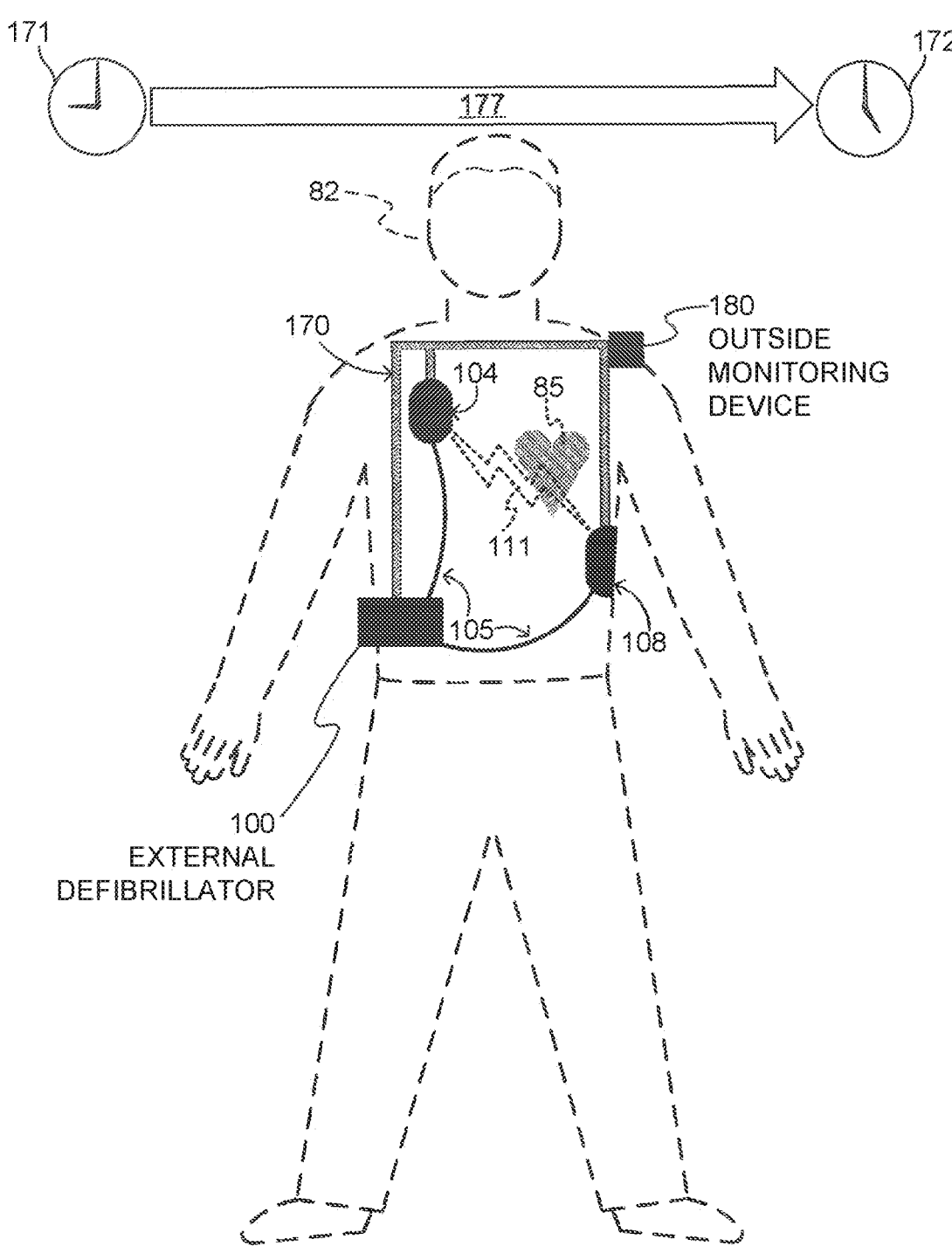
FIG. 1 is a diagram of components of a sample wearable cardioverter defibrillator (WCD) system made according to embodiments, and which is worn over many hours.

FIG. 1 depicts a patient 82. Patient 82 may also be referred to as a person and/or wearer, since the patient is wearing components of the WCD system. Patient 82 is ambulatory, which means that, while wearing the wearable portion of the WCD system, patient 82 can walk around and is not necessarily bed-ridden. While patient 82 may be considered to be also a "user" of the WCD system, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD system according to embodiments can be configured to defibrillate the patient who is wearing the designated parts the WCD system. Defibrillating can be by the WCD system delivering an electrical charge to the patient's body in the form of an electric shock. The electric shock can be delivered in one or more pulses.

In particular, FIG. 1 also depicts components of a WCD system made according to embodiments. One such component is a support structure 170 that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

In addition, FIG. 1 depicts patient 82 wearing the WCD system components over a long time duration 177. In this example, duration 177 is shown as starting at a time indication 171 of 9 o'clock, and ending at a time indication 172 of 5 o'clock, which can be the working hours of ambulatory patient 82.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

FIG. 1 shows a sample external defibrillator 100. As described in more detail later in this document, some aspects of external defibrillator 100 include a housing and an energy storage module within the housing. As such, in the context of a WCD system, defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 1 also shows sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 100 can be considered coupled to support structure 170 directly, or indirectly via at least one of defibrillation electrodes 104, 108.

When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A prior art defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also called physiological inputs and patient inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

Figure 2:
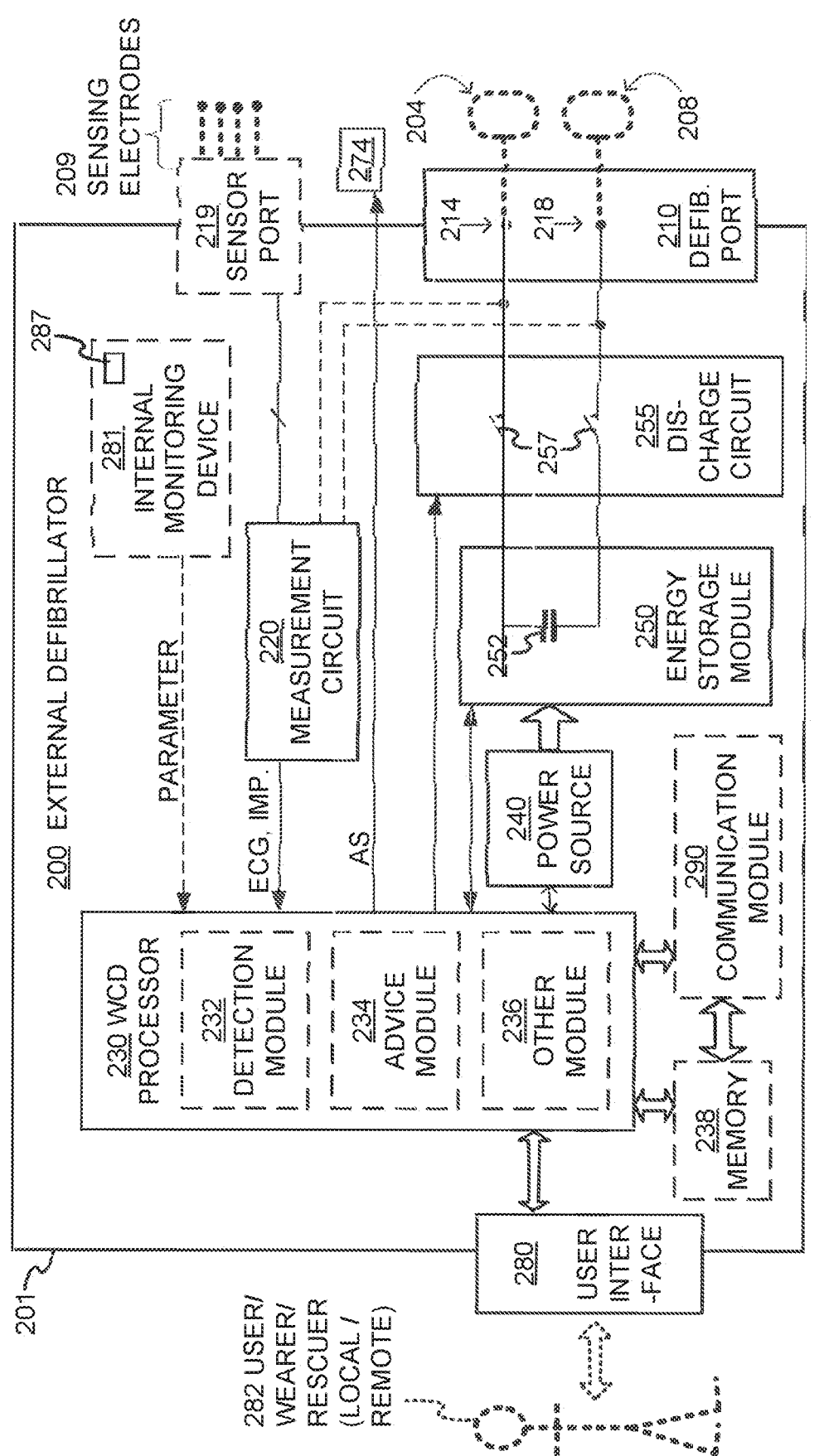
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as ambulatory patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors, as also described elsewhere in this document.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of patient 282. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$, $CO_2$, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may thus include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281. A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, which can be a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. As with defibrillation electrodes 204, 208, the support structure can be configured to be worn by patient 282 so as to maintain sensing electrodes 209 on a body of patient 282. For example, sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for both defibrillation electrodes 204, 208, and for sensing electrodes 209.

The fluid may be initially stored in a fluid reservoir, not shown in FIG. 2. Such a fluid reservoir can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations to which electrodes 204, 208 are configured to be attached to the patient. In some embodiments, fluid deploying mechanism 274 is activated prior to the electrical discharge responsive to receiving activation signal AS from a processor 230, which is described more fully later in this document.

In some embodiments, defibrillator 200 also includes a measurement circuit 220, as one or more of its modules working together with its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the input reflects an ECG measurement. The patient parameter can be an ECG, which can be sensed as a voltage difference between electrodes 204, 208. In addition, the patient parameter can be an impedance, which can be sensed between electrodes 204, 208 and/or between the connections of sensor port 219 considered pairwise. Sensing the impedance can be useful for detecting, among other things, whether these electrodes 204, 208 and/or sensing electrodes 209 are not making good electrical contact with the patient's body. These patient physiological signals may be sensed when available. Measurement circuit 220 can then render or generate information about them as inputs, data, other signals, etc. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. More strictly speaking, the information rendered by measurement circuit 220 is output from it, but this information can be called an input because it is received as an input by a subsequent device or functionality.

Defibrillator 200 also includes a processor 230, which is also called a WCD processor so as to distinguish from other processors in this description. Processor 230 may be implemented in a number of ways. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or values of other signals, may be used by the VF detector to determine whether the patient is experiencing VF. Detecting VF is useful, because VF typically results in SCA. Detection module 232 can also include a Ventricular Tachycardia (VT) detector for detecting VT, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments, and determine whether or not a shock criterion is met. The determination can be made from a rhythm analysis of the captured ECG signal or otherwise. For example, there can be shock decisions for VF, VT, etc.

In some embodiments, when the determination is to shock, an electrical charge is delivered to the patient. Delivering the electrical charge is also known as discharging and shocking the patient. As mentioned above, such can be for defibrillation, pacing, and so on.

In perfect conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in U.S. patent application Ser. No. 16/037,990, filed on Jul. 17, 2018 and since published as US 2019/0030351 A1, and also in U.S. patent application Ser. No.

16/038,007, filed on Jul. 17, 2018 and since published as US 2019/0030352 A1, both by the same applicant and incorporated herein by reference.

Processor 230 can include additional modules, such as other module 236, for other functions. In addition, if internal monitoring device 281 is indeed provided, processor 230 may receive its inputs, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or be stored there after it is received by defibrillator 200.

In embodiments, processor 230 may analyze short segments of the sensed ECG signal, and memory 238 may store WCD system data about the sensed ECG signal. Types of such WCD data are described later in this document. The stored WCD system data may be from at least one hour of the sensed ECG signal, for example the multiple hours of duration 177. It will be understood that gaps in data may exist in the sensed ECG signal or subsequently computed aspects, over that one hour or multiple hours of duration 177.

Defibrillator 200 can optionally include a communication module 290, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. Appropriate components may be included to provide for charging or replacing power source 240. In some embodiments, power source 240 is controlled and/or monitored by processor 230.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

A decision to shock can be made responsive to the shock criterion being met, as per the above-mentioned determination. When the decision is to shock, processor 230 can be configured to cause at least some or all of the electrical charge stored in module 250 to be discharged through patient 82 while the support structure is worn by patient 82, so as to deliver a shock 111 to patient 82.

For causing the discharge, defibrillator 200 moreover includes a discharge circuit 255. When the decision is to shock, processor 230 can be configured to control discharge circuit 255 to discharge through the patient at least some of all of the electrical charge stored in energy storage module 250. Discharging can be to nodes 214, 218, and from there to defibrillation electrodes 204, 208, so as to cause a shock to be delivered to the patient. Circuit 255 can include one or more switches 257. Switches 257 can be made in a number of ways, such as by an H-bridge, and so on. Circuit 255 could also be thus controlled via processor 230, and/or user interface 280.

A time waveform of the discharge may be controlled by thus controlling discharge circuit 255. The amount of energy of the discharge can be controlled by how much energy storage module has been charged, and also by how long discharge circuit 255 is controlled to remain open.

Defibrillator 200 can optionally include other components.

Figure 3:
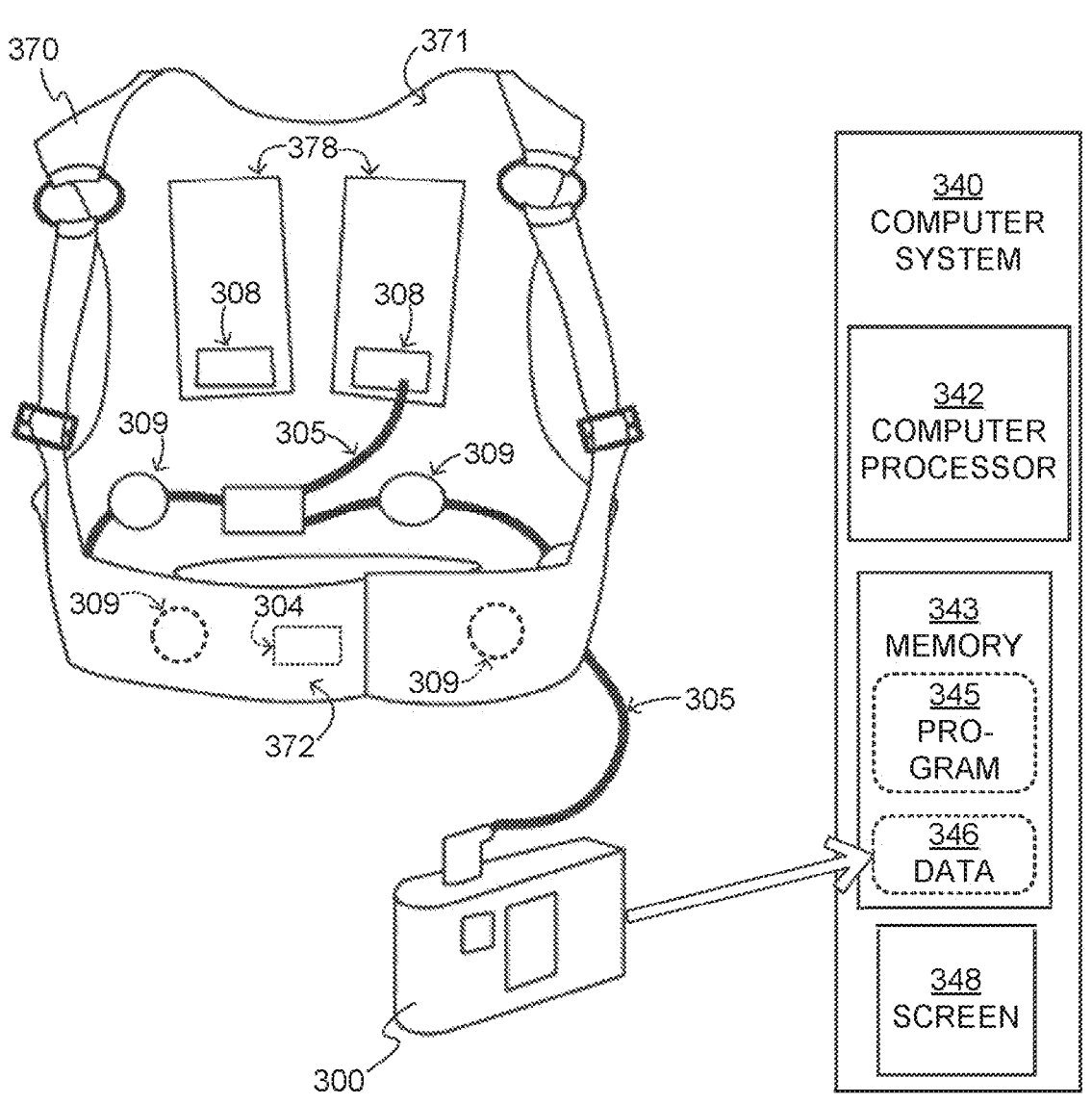
FIG. 3 is a diagram of sample embodiments of components of a WCD system, where further WCD stored data is downloaded to a computer system made according to embodiments.

FIG. 3 is a diagram of sample embodiments of components of an WCD system, along with a block diagram of a computer system 340 made according to embodiments. Computer system 340 includes a processor 342, which is also called a computer processor so as to distinguish from other processors in this description. Computer system 340 also includes a memory 343, which can be a non-transitory computer-readable storage medium. Memory 343 may store a sample program 345, or more than one such programs. When such one or more programs are executed by processor 342, they result in operations according to embodiments that are described later in this document. In addition, computer system 340 may have a screen 348, where data 346 is displayed, and so on. A person looking at screen 348 is therefore helped with monitoring the patient, and especially with monitoring the patient's long-term heart rate.

In FIG. 3, a support structure 370 includes a vest-like wearable garment. Support structure 370 has a back side 371, and a front side 372 that closes in front of the chest of the patient.

The WCD system of FIG. 3 also includes an external defibrillator 300. FIG. 3 does not show any support for external defibrillator 300, which may be carried in a purse, on a belt, by a strap over the shoulder, and so on. Wires 305 connect external defibrillator 300 to electrodes 304, 308, 309. Of those, electrodes 304, 308 are defibrillation electrodes, and electrodes 309 are ECG sensing electrodes.

Support structure 370 is configured to be worn by the ambulatory patient so as to maintain electrodes 304, 308, 309 on a body of the patient. Indeed, back defibrillation electrodes 308 are maintained in pockets 378. Of course, the inside of pockets 378 can be made with loose netting, so that electrodes 308 can contact the back of the patient, especially with the help of the conductive fluid that has been deployed. In addition, sensing electrodes 309 are maintained in positions that surround the patient's torso, for sensing ECG signals and/or the impedance of the patient. Sensing electrodes 309 are also called ECG electrodes.

Defibrillator 300 may have a processor like processor 230, and a memory like memory 238. As such, defibrillator 300 could also be storing WCD system data that is generated from at least one hour of the sensed ECG signal. This stored WCD system data can be about patient 82, according to embodiments. This stored WCD system data may be downloaded as data 346 into memory 343 of computer system 340. As such, computer system 340 may receive the stored WCD system data, process it, and even display it, as will be described in more detail later in this document.

ECG signals in a WCD system may include too much electrical noise to be useful. For a more robust operation, multiple ECG sensing electrodes 309 are provided, for presenting many options to processor 230. These options are different vectors for sensing the ECG signal, as described now in more detail.

Figure 4:
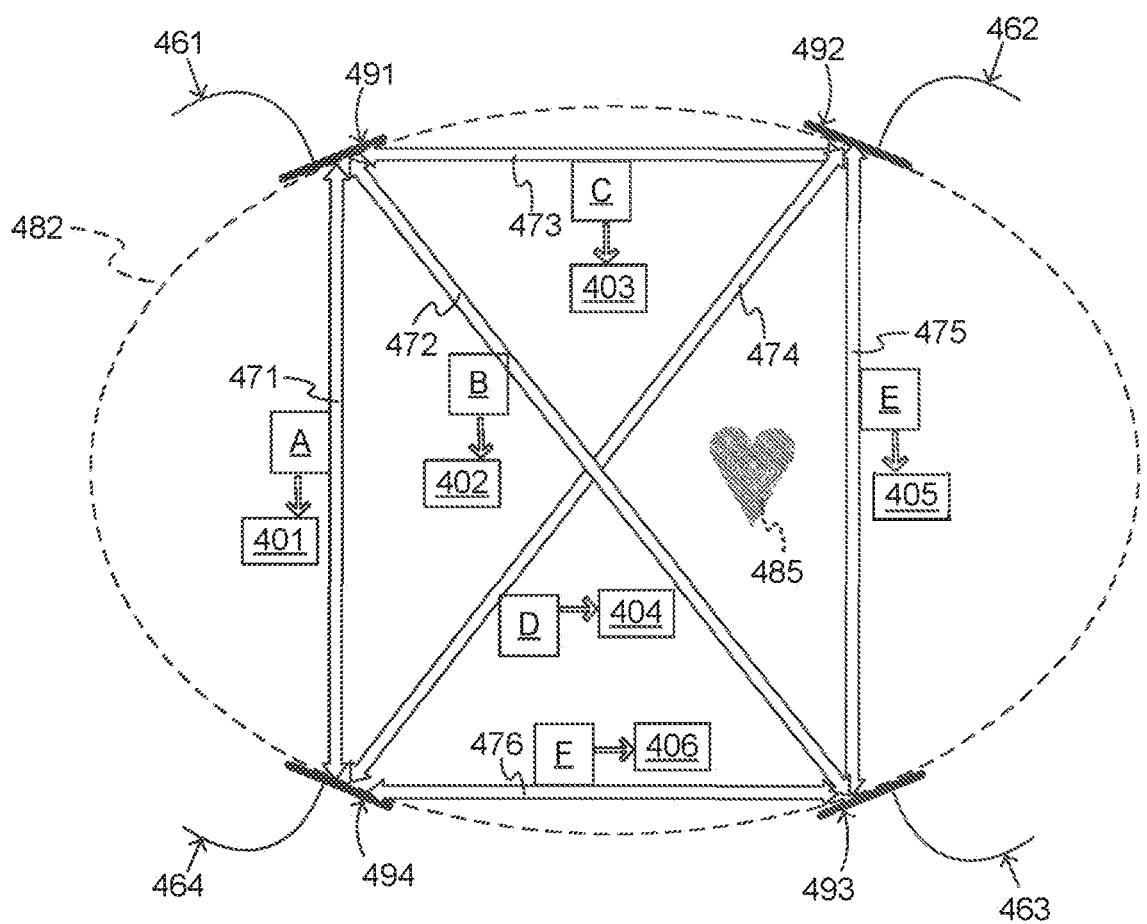
FIG. 4 is a conceptual diagram for illustrating an example how multiple ECG electrodes may be used for sensing ECG signals along different vectors in a WCD system according to embodiments.

FIG. 4 is a conceptual diagram for illustrating how multiple electrodes of a WCD system may be used for sensing ECG signals along different vectors according to embodiments. A section of a patient 482 having a heart 485 is shown. In FIG. 4, patient 482 is viewed from the top, patient 482 is facing downwards, and the plane of FIG. 4 intersects patient 482 at the torso of the patient.

Four ECG sensing electrodes 491, 492, 493, 494 are maintained on the torso of patient 482, and have respective wire leads 461, 462, 463, 464. It will be recognized that electrodes 491, 492, 493, 494 surround the torso, similarly with sensing electrodes 309 in the example of FIG. 3.

Any pair of these four ECG sensing electrodes 491, 492, 493, 494 defines a vector, along which an ECG signal may be sensed and/or measured. As such, electrodes 491, 492, 493, 494 define six vectors 471, 472, 473, 474, 475, 476. FIG. 4 thus illustrates a multi-vector embodiment.

These vectors 471, 472, 473, 474, 475, 476 define channels A, B, C, D, E, F respectively. In FIG. 4 it will be understood that electrodes 491, 492, 493, 494 are drawn as being on the same plane for simplicity and as is preferred, while that is not necessarily the case. Accordingly, vectors 471, 472, 473, 474, 475, 476 are not necessarily on the same plane, either.

Concurrent ECG signals 401, 402, 403, 404, 405, 406 may thus be sensed and/or measured from channels A, B, C, D, E, F, respectively, and in particular from the appropriate pairings of wire leads 461, 462, 463, 464 for each channel. It will be recognized that these ECG signals 401, 402, 403, 404, 405, 406 are concurrent versions of the ECG signal of patient 82 from the respective channels A, B, C, D, E, F. Short segments of these may be extracted and analyzed as also described elsewhere in this document.

In embodiments, in order to make the shock/no-shock determination as correctly as possible, a WCD may assess which of ECG signals 401, 402, 403, 404, 405, 406 is best for rhythm analysis and interpretation. For example, ECG signals that have the most noise may be ignored, discarded, not considered, while leaving the remaining ECG signals as candidates for making the shock/no shock determination.

Figure 5:
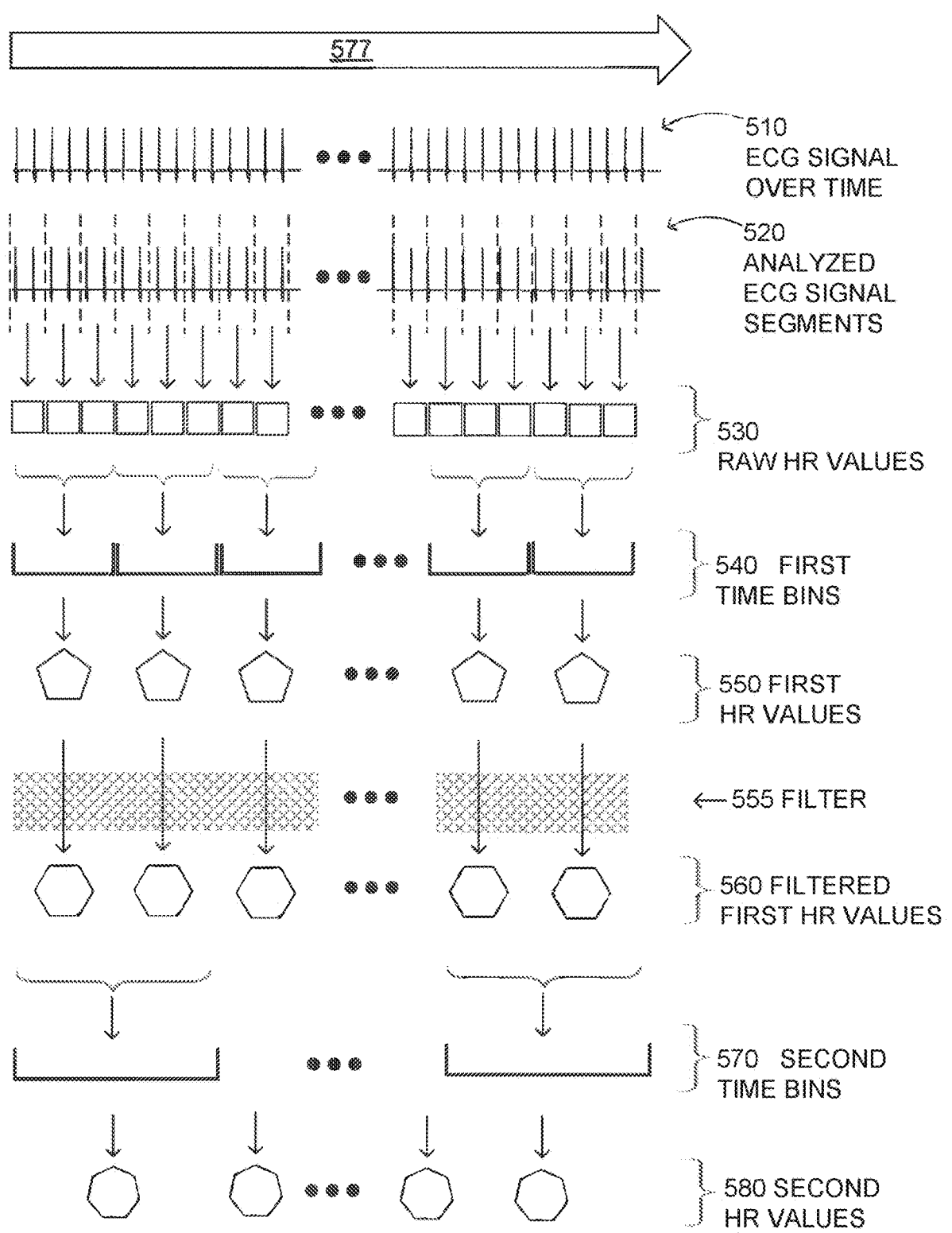
FIG. 5 shows time diagrams to illustrate the time evolution over a long term of a number of aspects according to embodiments.

FIG. 5 shows time diagrams to illustrate the time evolution of a number of aspects over a long-term duration 577. Duration 577 may be the same as duration 177.

In FIG. 5, a sample ECG signal 510 is shown. ECG signal 510 may have been sensed from patient 82 for over one hour, more hours, and so on.

As mentioned previously, ECG signal 510 may be analyzed in short segments. This is shown in waveform 520, where ECG signal 510 is shown divided in short segments. The short segments may have a suitable duration. A good value for that duration is approximately 4.8 sec.

Additional aspects of FIG. 5 will be also described with reference to methods.

The devices and/or systems mentioned in this document may perform functions, processes, acts, operations, actions and/or methods. These functions, processes, acts, operations, actions and/or methods may be implemented by one or more devices that include logic circuitry. A single such device can be alternately called a computer, and so on. It may be a standalone device or computer, such as a general-purpose computer, or part of a device that has and/or can perform one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description may include flowcharts, display images, algorithms, and symbolic representations of program operations within at least one computer readable medium. An economy may be achieved in that a single set of flowcharts can be used to describe both programs, and also methods. So, while flowcharts describe methods in terms of boxes, they may also concurrently describe programs.

Methods are now described.

FIG. 6 shows a flowchart 600 for describing methods according to embodiments. According to an operation 625, stored WCD system data may be received, for example as seen in FIG. 3.

According to another, optional operation 630, computed raw heart rate (HR) values may be inputted for respective ones of the short ECG signal segments 520. The raw heart rate is also called short-term heart rate. Sample such raw HR values 530 are shown in FIG. 5. The computation may happen by different processors, as will be seen shortly. Operation 630 may be performed in a number of ways.

First, in some embodiments the stored WCD system data encodes amplitude values of the sensed ECG signal, such as ECG signal 510. In such embodiments, the method may further comprise the operation of computing, from the amplitude values, the raw HR values 530 that are subsequently inputted at operation 630. These raw HR values 530 may be thus computed by processor 342 of computer system 340. These raw HR values 530 can be computed from ECG peaks of the short ECG signal segments 520.

Second, in other embodiments, processor 230 further computes the raw HR values 530 of the short ECG signal segments 520. In such embodiments, the stored WCD system data includes the raw HR values that are subsequently inputted at operation 630.

In some of these embodiments, as seen in FIG. 3 and FIG. 4, there may be more than one ECG channels. In particular, the WCD system may further include a plurality of ECG electrodes 309, three or more channels A, B, C, D, E, F may be defined by the ECG electrodes, and three or more versions 401, 402, 403, 404, 405, 406 of the patient's ECG signal can be sensed from the three or more channels.

In such embodiments, processor 230 of the WCD system may analyze short segments of the three or more versions of the patient's ECG signal. In addition, a certain one of the inputted HR values for a certain short segment may be computed by: a) computing three or more respective tentative HR values from the three or more short segments of the three or more versions of the patient's ECG signal, and b) deriving the certain inputted HR value from at least one of the three or more respective tentative HR values. Such a derivation can be implemented in a number of ways. In some embodiments, the derivation is from a middlemost-ranked one of the three or more respective tentative HR values. The concept of a middlemost-ranked HR value is now explained, for odd-numbered sets and even-numbered sets of values.

Figures 7A, 7B:
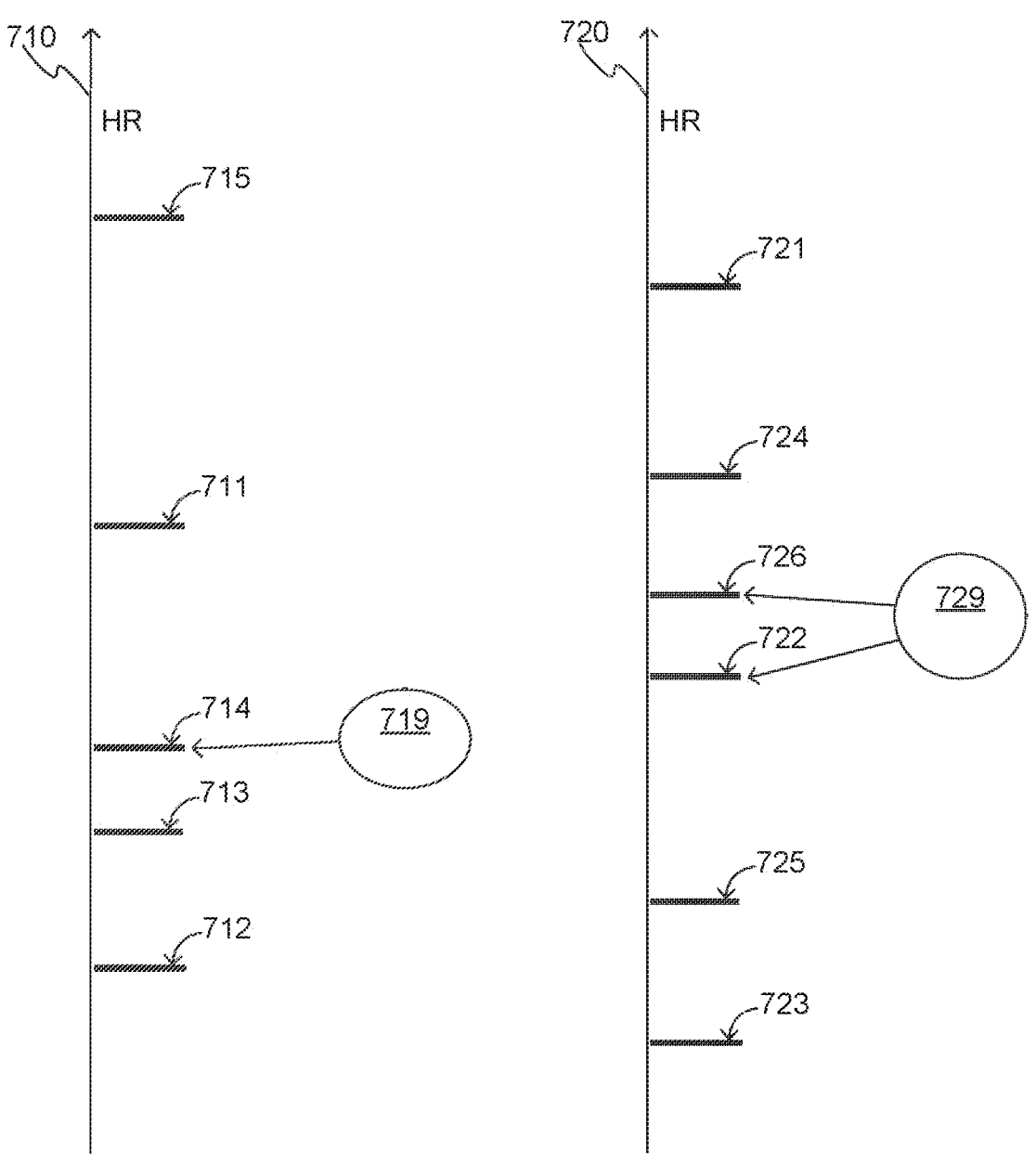
FIGS. 7A and 7B show sample sets of HR values plotted against HR axes in ways that result in ranking the HR values according to embodiments.

FIG. 7A shows an HR values axis 710. A sample set of HR values 711, 712, 713, 714, 715 are plotted against axis 710. This sample set has five HR values, which is an odd number. Such an odd number might occur if one of the six channels had too much noise for an HR value to be computed, or resulted in an HR value that is so suspect that it is not even considered. This example also assumes that, even though there is noise in one of the channels, there is no disqualification of the entire short segment due to noise. This assumption is not always true, according to embodiments.

The plotting on axis 710 results in the HR values being arranged according to their values. The arranging results in the following ranking of these HR values, from largest to smallest: 715, 711, 714, 713, 712. According to a comment 719, HR value 714 is the middle-most ranked, being the third among the five.

FIG. 7B shows an HR values axis 720. A sample set of HR values 721, 722, 723, 724, 725, 726 are plotted against axis 720. This sample set has six HR values, which is an even number. The plotting on axis 720 results in the HR values being arranged according to their values. The arranging results in the following ranking of these HR values, from largest to smallest: 721, 724, 726, 722, 725, 723. According to a comment 729, HR values 722 and 726 are the middle-most ranked, being the third and fourth among the six. Here there are two middle-most ranked HR values, because the set has an even number.

As such, the derivation of the certain inputted HR value from a middlemost-ranked one of the three or more respective tentative HR values can be implemented in a number of ways. In some embodiments, the certain inputted HR value is the middlemost-ranked tentative HR values. In other embodiments, the certain inputted HR value is derived from one the middlemost-ranked tentative HR values, for example by using a statistic such as an average.

Regarding the notion of a median, for FIG. 7A with an odd number of HR values, middle-most ranked HR value 714 is also the median. On the other hand, for FIG. 7B with an even number of HR values, neither one of the two middle-most ranked HR values 722 and 726 is the median, strictly speaking. Rather, the median in this case would be a numerical average of middlemost-ranked HR values 722 and 726, because this is an even-numbered set. Regardless, for purposes of embodiments where one of the middle-most ranked HR values is used for determining long-term heart rates, the approach can be called substantially-median-based determination.

Returning to FIGS. 5 and 6, according to another operation 640, groups of raw HR values 530 may be aggregated into respective first time bins 540. First time bins 540 can be arranged in a time sequence, for example according to the timing of ECG signal 510 along duration 577. It will be understood, then, that each first time bin includes a number of raw HR values 530, according to the duration of the short segments. First time bins 540 can be defined to have a suitable time duration. An example such time duration is approximately one minute, in which case each one-minute time bin will have about 24 raw HR values 530.

According to another operation 650, first HR values 550 may be derived for respective ones of first time bins 540. In some embodiments, the first HR value of a certain one of the first time bins is derived from a middlemost-ranked one of at least some of the raw HR values aggregated into the certain first time bin. As before, the first HR value of the certain first time bin can be one of the middlemost-ranked raw HR values aggregated into the certain first time bin. Or, that first HR value can be derived from it, for example by using a statistic such as an average. In some embodiments, the first HR values 550 of all first time bins 540 are derived from such a middlemost-ranked one of the raw HR values, and so on. In some embodiments, raw HR values that meet error conditions are first removed from a first time bin, and then first HR values 550 are derived from the values remaining in the bin. Sample error conditions are described elsewhere in this document.

In some embodiments, first time bins 540 may be cleaned up from seemingly errant computed raw HR values 530 before first HR values 550 are derived. For example, from a certain first time bin a certain computed raw heart rate (HR) value may be discarded if it meets an error condition. In such embodiments, then, the first HR values are derived from at least some of the raw HR values aggregated and remaining into the certain first time bin after the discarding. In other words, the middlemost-ranked raw HR value may be derived from the raw HR values aggregated and remaining into the certain first time bin after the discarding, and so on.

A number of error conditions are possible. For instance, the certain computed raw HR value may meet the error condition when it differs from another raw HR value aggregated into the certain first time bin by at least an error HR threshold, while no two other raw HR values aggregated into the certain first time bin differ from each other by as much as the error HR threshold, only less. This error condition may succeed in discarding outlier raw HR values, before first HR values 550 are derived. Other possible error conditions are described later in this document.

Another, optional operation 660 may take place using a filter 555, to result in filtered or adjusted first HR values 560. This filtering is also called adjusting. According to operation 660, a certain one or more of the first HR values 550 of a certain one or more of first time bins 540 is adjusted or filtered. Adjusting can be performed in a number ways, which are described later in this document.

According to another, optional operation 670, groups of first time bins 570 are aggregated into respective second time bins 570. Second time bins 570 can be larger than first time bins 570, and in fact include a fixed number of them. Second time bins 570 have a suitable time duration. An example such time duration is approximately three minutes, for each to fit three first time bins. The example of FIG. 5 shows only two first time bins for each second time bin, but that is only due to space limitations in the drawing.

According to another operation 680, second HR values 580 may be derived for the respective second time bins 580. In some embodiments, the second HR value of a certain one of the second time bins is derived from a middlemost-ranked one of at least some of the first HR values of the first time bins that are aggregated into the certain second time bin. As before, the second HR value of the certain second time bin can be one of the middlemost-ranked first HR values of the first time bins that are aggregated into the certain second time bin. Or, that second HR value can be derived from it, for example by using a statistic such as an average. In some embodiments, second HR values 580 of all second time bins 570 are derived from such a middlemost-ranked one of first HR values 550, or adjusted/filtered first HR values 560.

According to another operation 690, second HR values 580 are then stored, for example in memory 238 or memory 343. As such, the stored second HR values that have been thus derived from the stored WCD system data may be from at least one hour of the sensed ECG signal, and hopefully the entire durations 577, 177.

According to another, optional operation 695, the stored second HR values are displayed, for example at screen 348, as is described in more detail later in this document.

Embodiments of filtering operation 660 are now described in more detail. In this filtering, HR values can adjusted in view of HR values that are nearby in the time sequence, namely their near neighbors. These can be their immediate, adjacent neighbors, or maybe more removed neighbors when filtering spans a range of broader than three time bins. This filtering is also called median filtering, at least where an odd numbered set of HR values are used, and the median of the defined range is chosen to plainly replace the certain HR value in question.

In general, before aggregating groups of first time bins 540 into second time bins 550, a certain one of the first HR values of a certain one of the first time bins may be adjusted or filtered. Such adjusting or filtering can be performed in a number of ways. One such way is in view of a first HR value of a first time bin that is within a filter range of the certain first time bin in the time sequence. Of course, in such cases, at least one of the first HR values of first time bins 540 that are aggregated into a certain second time bin 570 at operation 670 is the adjusted certain first HR value 560, instead of the first HR value 550 prior to the adjustment or filtering.

In embodiments, the adjusting is in view of adjacent first time bins in both directions, namely preceding and succeeding the certain first time bin in the time sequence. In such embodiments, a certain range is chosen centered on the certain time bin. First HR values are considered for the certain range, and adjusting includes replacing the certain first HR value by a middlemost-ranked one of the range.

In embodiments, the adjusting includes outright replacing the certain first HR value by an adjusted value, in which the adjustment value a) is derived from the first HR value of the first time bin that is adjacent to the certain first time bin in the time sequence, but b) is not derived from the certain first HR value. In other words, the certain first HR value does not contribute to the adjusted value with which it is replaced. And, in some of these embodiments, the adjusted value is plainly that first HR value of the first time bin that is immediately adjacent to the certain first time bin in the time sequence.

An example is now described, where all the first HR values are thus filtered by being potentially replaced by an adjusted value that is plainly an adjacent first HR value. The filtering range is three, which means that along with the certain value, there is only one preceding and only one succeeding neighbor considered. Since three is an odd number, the middlemost-ranked HR value of the range is also the median.

Figure 8A:
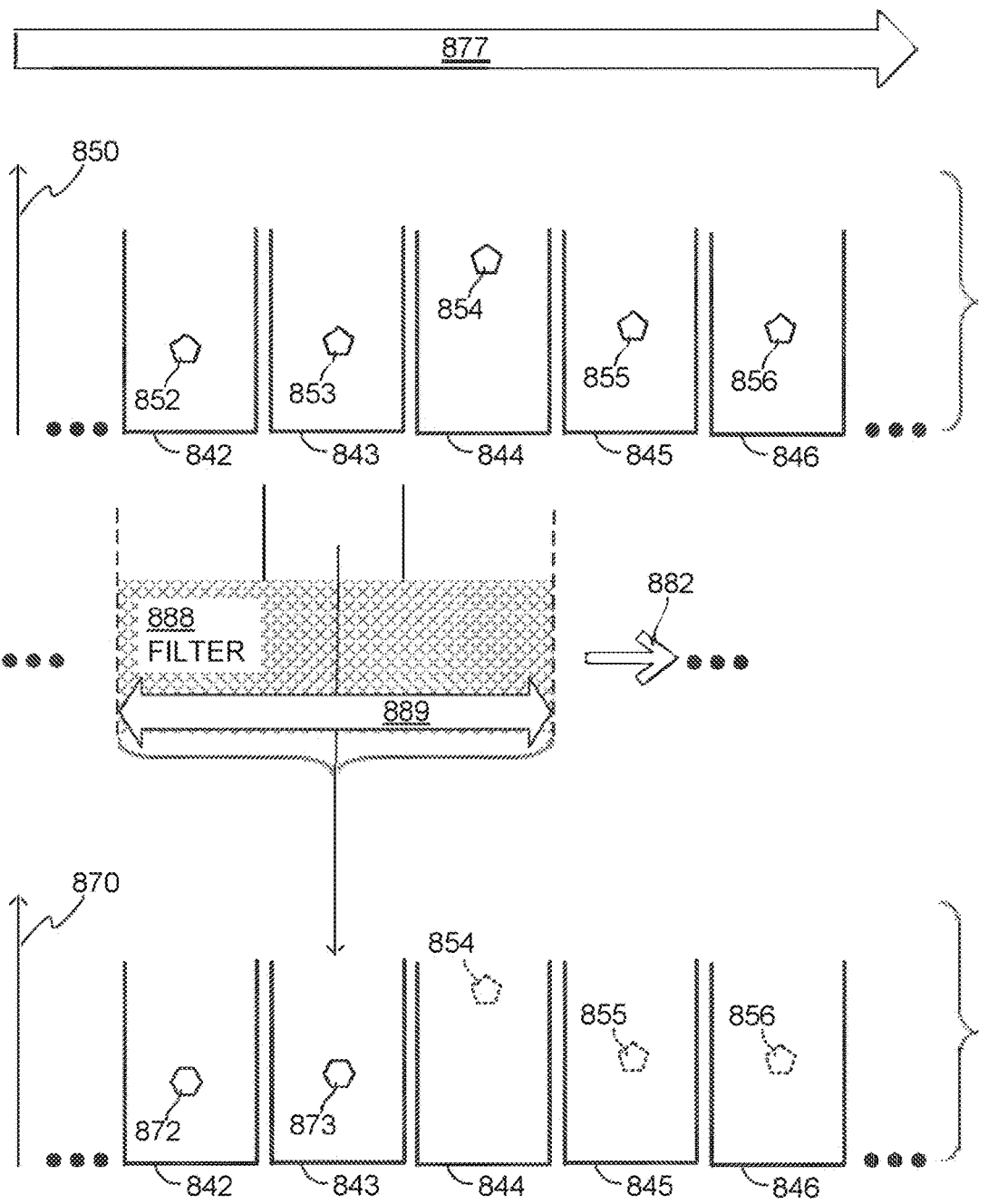
FIGS. 8A-8B-8C show successive snapshots of adjusting or filtering HR values according to embodiments.

Referring to FIG. 8A, in the upper portion of the drawing, sample first time bins 842, 843, 844, 845, 846 are shown in a time sequence, along a time duration 877. Time duration 877 can be, for example, time duration 577 and/or time duration 177.

For these first time bins 842, 843, 844, 845, 846, first HR values 852, 853, 854, 855, 856, have been derived, for example as described above. In addition, an axis 850 is shown, similar to axes 710, 720. First HR values 852, 853, 854, 855, 856 are shown a) within their respective first time bins 842, 843, 844, 845, 846, and concurrently also b) having a height that corresponds to their value against axis 810. It will be observed that first HR value 854 has the highest value along axis 850, while the values of the others are more clustered.

A filter 888 is shown, which can also be filter 555. Filter 888 has a range 889, which spans three of the first time bins at a time. In FIG. 8A, filter 888 is centered on first time bin 843, which is thus the certain first time bin for FIG. 8A. Filter 888 has gotten to this position by moving to the right along the time sequence, as shown by an arrow 882. Given this position, for certain first time bin 843, filter 888 considers the first time bins within its range 889, namely first time bin 843, immediately preceding first time bin 842, and immediately succeeding first time bin 844.

In the lower portion of FIG. 8A, sample first time bins 842, 843, 844, 845, 846 are repeated. A vertical axis 870 shows HR values. Within first time bins 842, 843 are shown filtered values 872, 873, resulting from first HR values 852, 853. In this example, filtered values 872, 873, are identical to first HR values 852, 853. Also, within first time bins 844, 845, 846 are shown-dotted only for comparison-original first HR values 854, 855, 856, but filtering has not yet taken place for them.

Figure 8B:
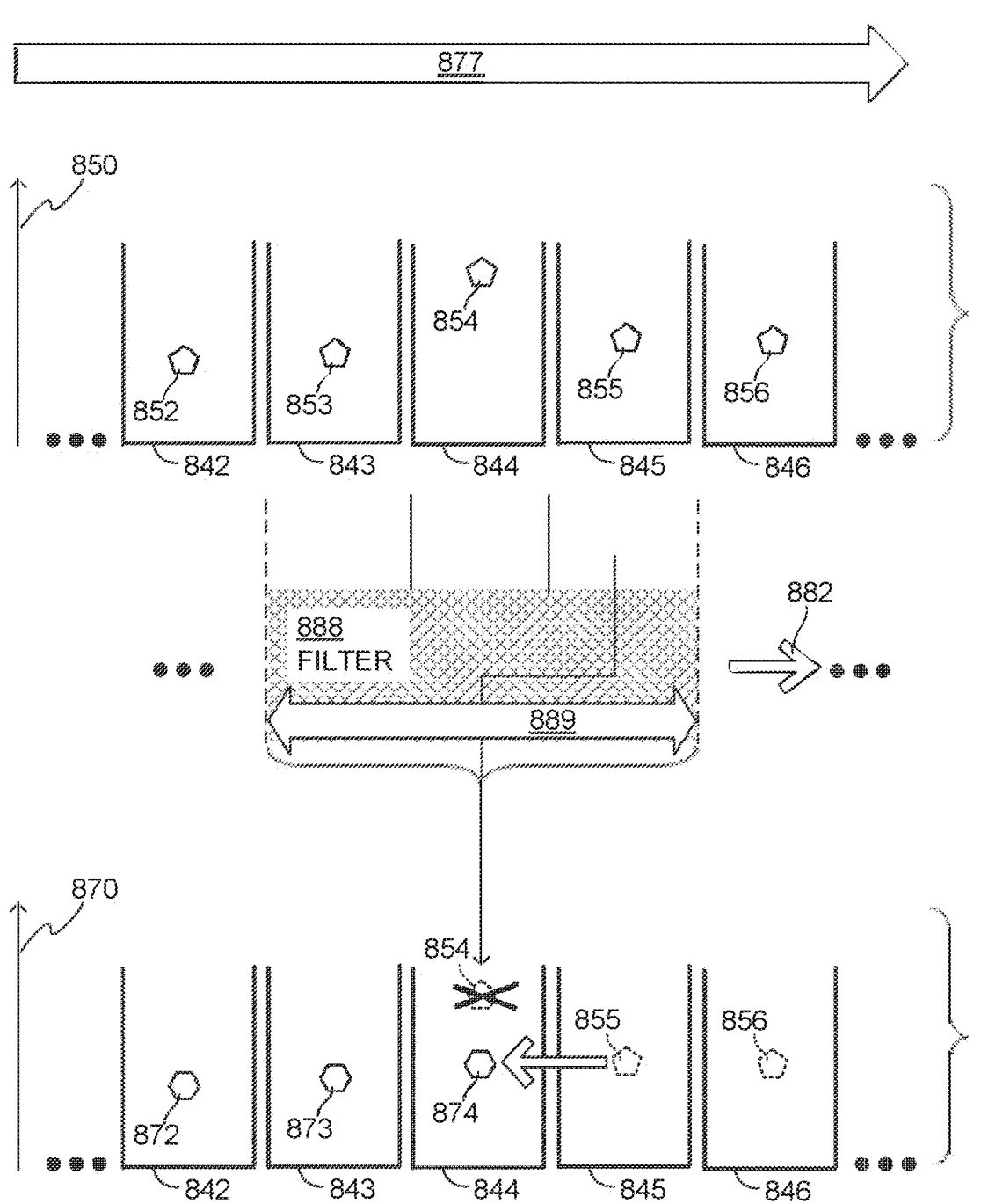

FIG. 8B shows the arrangement of FIG. 8A, except that filter 888 has moved by one, and is now centered on the next first time bin 844. In addition, new filtered value 874 has replaced former first HR values 854, by operation of filter 888. It will be observed that new filtered HR value 874 equals HR value 855, which is the median of values 852, 853, 854 of first time bins 843, 844, 845 that are in the current range 889 of filter 888. Filtered HR value 874 is thus the adjusted HR value that HR value 855 has been plainly replaced by. And it will be observed that filtered HR value 874 appears closer to its neighbors in the lower portion of the diagram, than first HR value 854 appears with respect to its own neighbors.

Figure 8C:
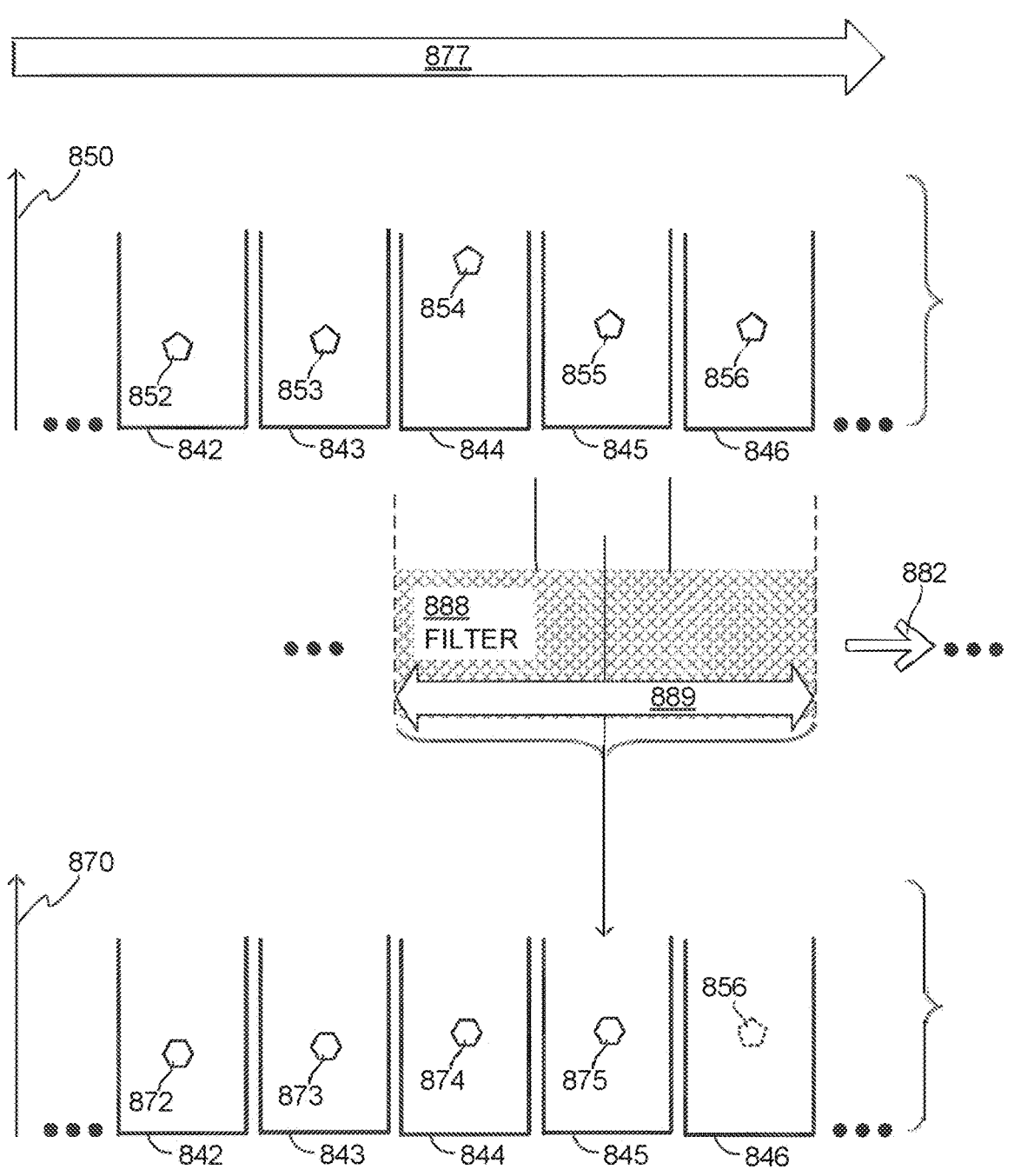

FIG. 8C shows the arrangement of FIG. 8B, except that filter 888 has further moved by another one, and is now centered on the next first time bin 845. In addition, new filtered value 875 is the same as first HR value 855, by operation of filter 888. In this instance, there was no replacing.

FIG. 9 shows a flowchart 900 for describing methods according to embodiments. Operations 925, 930, 940 may be performed as operations 625, 630, 640 respectively. Operation 950 may be performed as operation 650, or in different ways.

At another operation 960, at least one, and maybe some of the first HR values may be replaced by adjusted first HR values. An example was seen in FIG. 8B, where first HR value 854 was adjusted, filtered by being replaced with by an adjusted first HR value. In that case, the adjusted first HR value was an HR value derived from HR value 854 that was within filter range 889 of filter 888, and in fact it was plainly HR value 854 itself.

Additional operations may be further performed, for example to derive second HR values from the first HR values. Such additional operations may be performed in a number of ways, for example as described with reference to FIG. 6.

At another operation 990, at least some of the first HR values and the adjusted first HR values are stored, for example in memory 238 or in memory 343. Of course, if second HR values have been derived, they can be stored in lieu of the first HR values. In embodiments, the HR values thus stored at operation 990 have been thus derived from the stored WCD system data. In addition, that stored WCD system data may have been generated from at least one hour of the sensed ECG signal, and hopefully the entire durations 577, 177. And, at operation 995, the stored HR values may be displayed.

In some embodiments, provisions are made for HR values that are suspected of being in error. In such embodiments, raw HR values may be marked as error-prone. In addition, time bins may be marked as error-prone if they have included such error-prone raw HR values. Moreover, derived HR values for such time bin values may be marked as error-prone. Displaying may be affected also, according to embodiments. Examples are now described.

Figure 10:
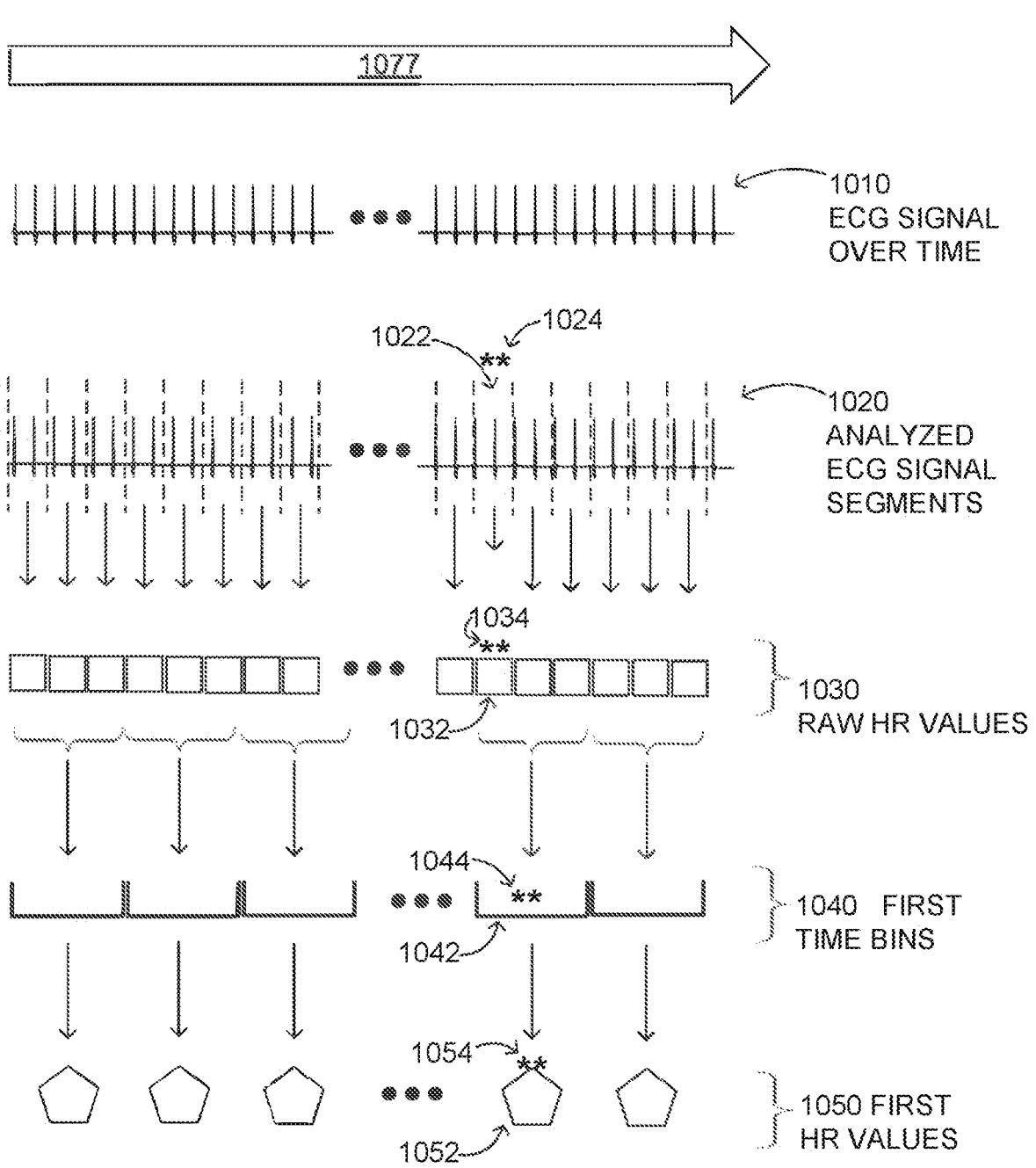
FIG. 10 shows time diagrams to illustrate the time evolution of a number of aspects over a long term where, for one of computed raw HR values an error condition is determined to be met according to embodiments.

Referring now to FIG. 10, the time evolution of a number of aspects is shown. It will be appreciated that FIG. 10 has a number of aspects similar to those of FIG. 5, and some of the description is similar. In FIG. 10 the time evolution is over a long-term duration 1077 which may be the same as durations 877, 577 or 177.

A sample ECG signal 1010 is shown, generally similar to ECG signal 510. As mentioned previously, ECG signal 1010 may be analyzed in short segments, as shown in waveform 1020. Resulting respective computed raw HR values 1030 are also shown. Furthermore, groups of raw HR values 1030 are aggregated into respective first time bins 1040, and first HR values 1050 are derived for respective first time bins 1040. These first HR values 1050 may be derived from at least some of raw HR values 1030 aggregated into each first time bin.

In this example, an error condition is determined to be met for a certain one of the first HR values, namely first HR value 1052. This determination may be made by processor 230 of the WCD system, or processor 342.

As such, in this example, first HR value 1052 is marked as error-prone, with a marking 1054. Optionally, earlier aspects in this progression may be also marked as error-prone, depending on the embodiment. For example, first time bin 1042 for which first HR value 1052 was derived may also be marked as error-prone, with a marking 1044. In some embodiments, computed raw HR value 1032, which was aggregated into first time bin 1042, is also be marked as error-prone with a marking 1034. In some embodiments, ECG short segment 1022, which was considered and/or used and/or contributed to what was aggregated into first time bin 1042, is also be marked as error-prone with a marking 1024. In some embodiments, of course, the error may be so large as to prevent the computation of an raw HR value, or it may permit the computation but result in an raw HR value that has a simply unrealistic value that can be safely disregarded.

A number of error conditions are possible. Examples are now described.

In some embodiments, the error condition is related to disparity of raw HR values 1030 that are being aggregated into a single first time bin 1042. In such embodiments, the error condition may include that the certain first HR value 1052 is derived from a certain one of the first time bins, in which the certain first time bin 1042 aggregates a group of the raw HR values of which one is larger than another one by at least an error HR threshold. A useful value for the error HR threshold is about 10%.

In some embodiments that have multiple ECG electrodes, the error condition can include that one of the ECG electrodes is detected to be off, meaning detached from the patient's body. This can be detected in a number of ways, such as by the lack of two or more versions of the patient's ECG signal.

In some embodiments that have multiple ECG electrodes, the error condition can include that, in at least one of the versions, a detected noise exceeds a noise threshold. There are a number of ways of defining a channel as noisy according to embodiments: 1) pctAmp—percentage of QRS complexes that are too large in amplitude, 2) pctBS—percent baseline shift, or the percentage of a segment that has too large of a shift from zero amplitude, 3) dPW—peak width, which is classified as noisy if there are too narrow of peaks, and 4) dZC—zero crossings, which is defined as noisy if the signal crosses 0 too many times in a given timeframe. Any one of these variables can signal a noisy channel, by itself or in combination with others.

FIG. 11 shows a flowchart 1100 for describing methods according to embodiments. Operations 1125, 1130, 1140, 1150 may be performed as operations 925, 930, 940, 950 respectively.

At another operation 1165, at least one, and maybe some of the first HR values may be marked as error-prone. An example was seen in FIG. 10, where first HR value 1052 was marked by a marking 1054.

At another operation 1190, at least some of the first HR values are stored, for example in memory 238 or memory 343. In embodiments, the thus stored HR values have been thus derived from the stored WCD system data which, in turn may be generated from at least one hour of the sensed ECG signal, and hopefully the entire duration 1077.

And, at operation 1195, the stored first HR values may be displayed. The stored first HR values for which the error condition was not determined to be met can be displayed in a first manner. On the other hand, the stored first HR values for which the error condition was determined to be met can be displayed in a second manner that is different from the first manner the certain first HR value, for example to indicate a due lack of confidence in the result.

In some embodiments, the second manner includes displaying error indicia in relation to the certain first HR values for which the error condition was determined to be met. An example is now described.

Figure 12:
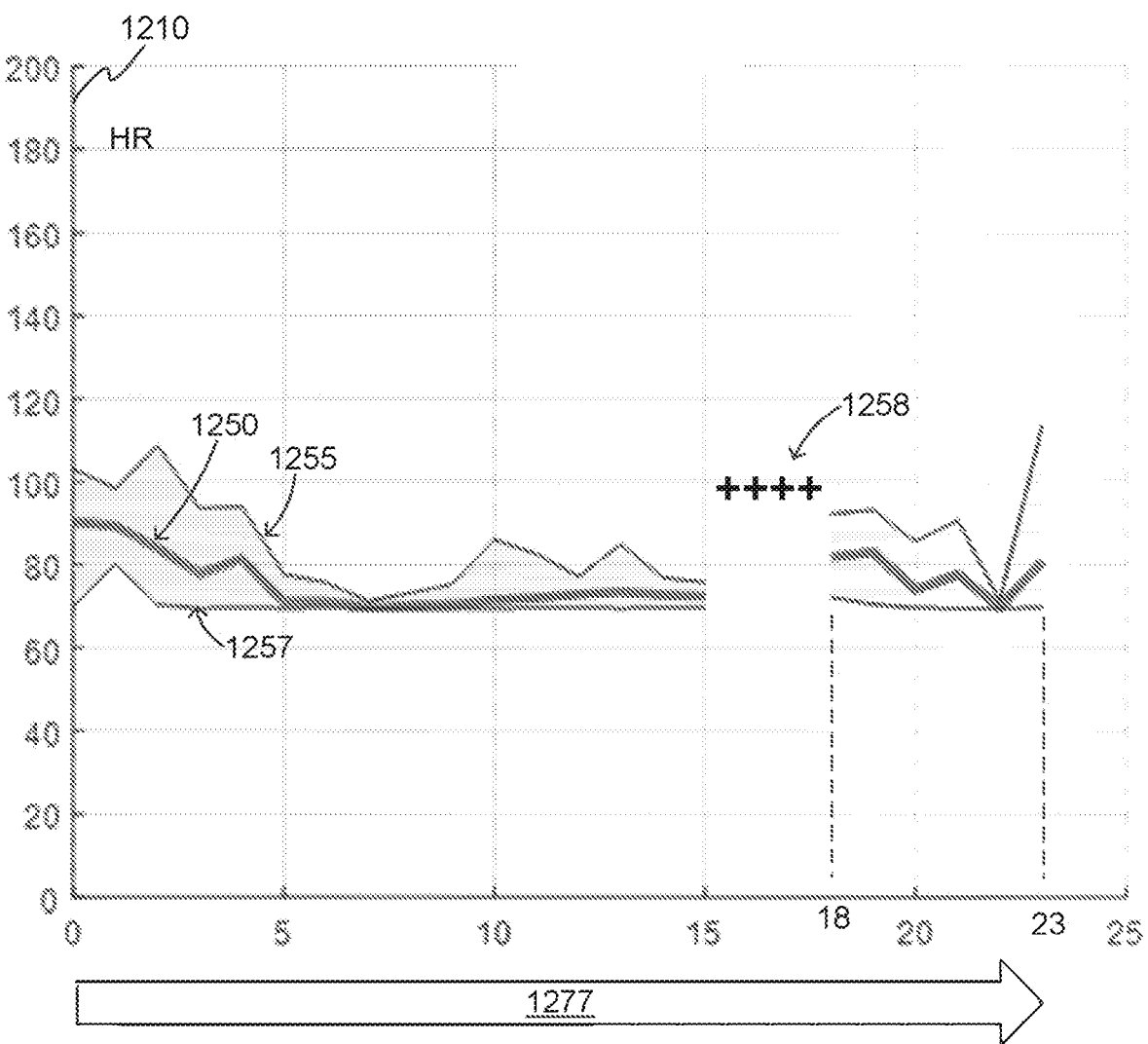
FIG. 12 is a diagram of a sample displayed long-term heart rate of a patient, according to embodiments.

Referring now to FIG. 12, a vertical axis 1210 indicates final heart rate values, which can be the first heart rate values, second heart rate values, and so on. A time duration 1277 is parallel to a horizontal axis that is demarcated in hours.

A diagram of a sample displayed long-term heart rate of a patient is indicated by a line 1250. In this example, additionally a maximum 1255 and a minimum 1257 lines are also shown. This display between hours 0-15 and 18-23 is regarded as a first manner of displaying. At least some the stored HR values are thus displayed concurrently.

In this example, first HR values between hours 15-18 have been marked as error-prone, and are not displayed at all. Instead, error indicia 1258 is displayed near where these first HR values would be displayed.

In other embodiments, the second manner includes not displaying at all the certain first HR values for which the error condition was determined to be met. An example is now described.

Figure 13:
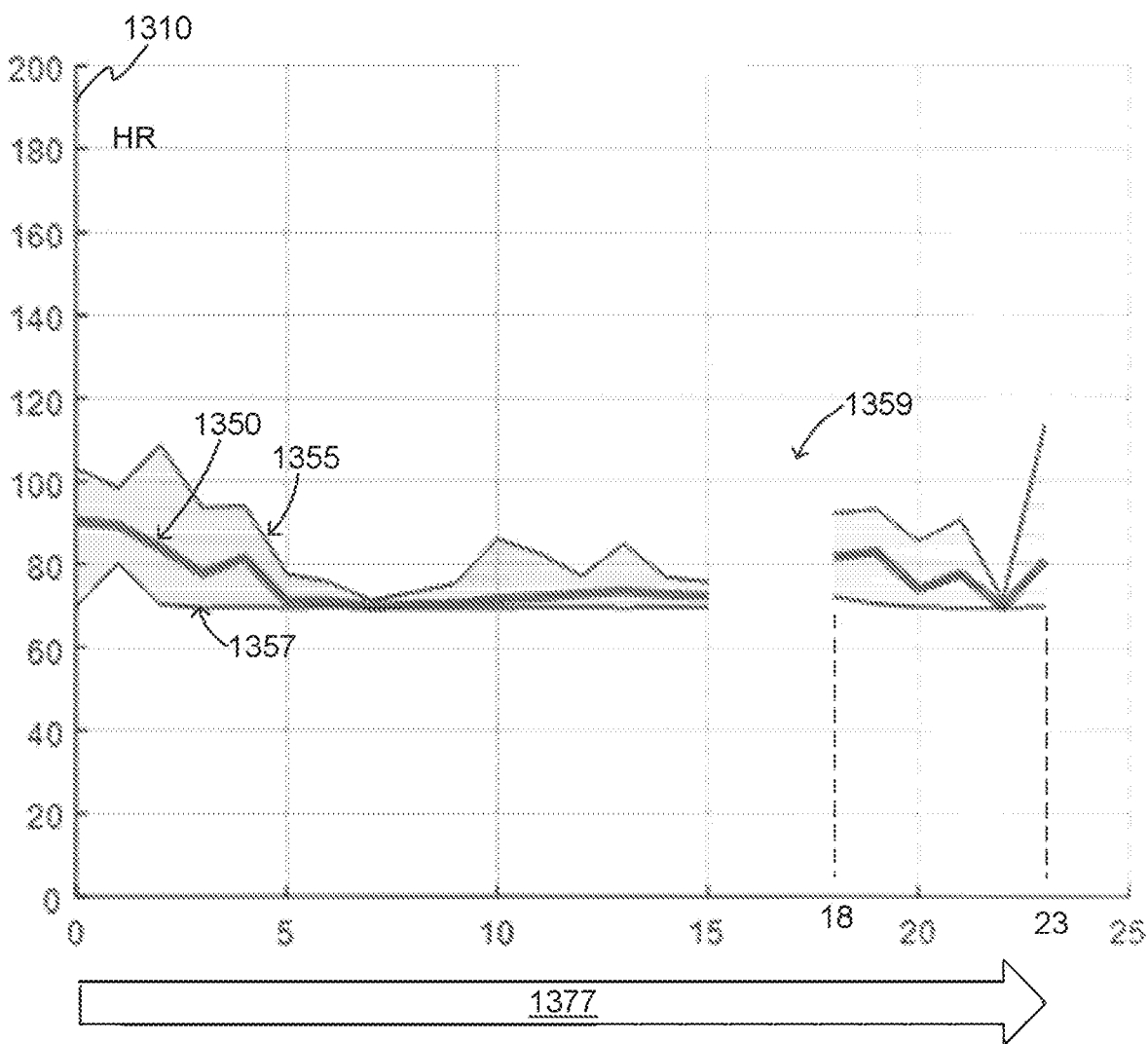
FIG. 13 is a diagram of a sample displayed long-term heart rate of a patient, according to other embodiments.

Referring now to FIG. 13, a vertical axis 1310 indicates final heart rate values, which can be the first heart rate values, second heart rate values, and so on. A time duration 1377 is parallel to a horizontal axis that is demarcated in hours.

A diagram of a sample displayed long-term heart rate of a patient is indicated by a line 1350. In this example, additionally a maximum 1355 and a minimum 1357 lines are also shown. This display between hours 0-15 and 18-23 is regarded as a first manner of displaying. At least some the stored HR values are thus displayed concurrently. In this example, first HR values between hours 15-18 are not displayed at all, leaving a gap 1359.

In other instances, a gap such as gap 1359 is left from a time that the patient is not wearing the WCD system.

In some embodiments, a wearable medical monitor (WMM) system has aspects similar to those of a WCD system, except it does not include the defibrillator and the defibrillator electrodes. For example, FIG. 14 is a diagram of sample embodiments of components of an WMM system, along with a block diagram of a computer system 1440 made according to embodiments. Accordingly, embodiments provide long-term heart rate trend from multi-channel ECG data of wearable medical monitor. Of course, a WCD system according to embodiments is also a type of a wearable medical monitor system. And all embodiments may discard error data.

Computer system 1440 can be similar in many ways to computer system 340 of FIG. 3. Computer system 1440 includes a processor 1442, which is also called a computer processor, and a memory 1443, which can be a non-transitory computer-readable storage medium. Memory 1443 may store a sample program 1445, or more than one such programs. When such one or more programs are executed by processor 1442, they result in operations according to embodiments that are described later in this document. In addition, computer system 1440 may have a screen 1448, where data 1446 is displayed, and so on. A person looking at screen 1448 is therefore helped with monitoring the patient, and especially with monitoring the patient's long-term heart rate.

In FIG. 14, a support structure 1470 includes a vest-like wearable garment. Support structure 1470 has a back side 1471, and a front side 1472 that closes in front of the chest of the patient.

The WMM system of FIG. 14 also includes a device 1400. FIG. 14 does not show any support for device 1400, which may be carried in a purse, on a belt, by a strap over the shoulder, and so on. Wires 1405 connect device 1400 to ECG electrodes 1409.

Support structure 1470 is configured to be worn by the ambulatory patient so as to maintain electrodes 1409 on a body of the patient. In addition, sensing electrodes 1409 are maintained in positions that surround the patient's torso. The ECG electrodes thus define two or more channels and are configured to sense two or more versions of an ECG signal of the patient across the two or more channels.

Device 1400 may have a WMM processor and a memory such as was described for processor 230 and memory 238. As such, device 1400 could also be storing WMM system data that is generated from at least one hour of the sensed ECG signal. This stored WMM system data can be about patient 82, according to embodiments.

Device 1400 may also have a screen 1499. In some embodiments, all the processing is done by the WMM processor, and the results and graphs are displayed in screen 1499, without using computer system 1440 at all.

In some embodiments, this stored WMM system data may be downloaded as data 1446 into memory 1443 of computer system 1440. As such, computer system 1440 may receive the stored WMM system data, process it, and even display it, as will now be described.

FIG. 15 shows a flowchart 1500 for describing methods according to embodiments for WMM systems. Many concepts in this are similar to what is previously described.

An operation 1525 may be performed for a WMM system as operation 1125 for a WCD system. Operations 1530, 1540 may be performed as operations 1130, 1140 respectively.

According to another operation 1545, computed raw heart rate (HR) values that meet an error condition may be discarded from their respective bins. A number of error conditions are possible, some of which were described above.

According to another operation 1550 first HR values may be derived for respective ones of the first time bins. The discarded HR values are preferably not used here. The first HR value of a certain one of the first time bins can be derived from raw HR values aggregated and remaining into the certain first time bin after the discarding of operation 1545.

According to another, optional operation 1565, at least some first HR values are marking as error-prone, if these first HR values were derived for first time bins from which raw HR values were discarded. The more values discarded, the more error prone they may be. An example was seen in FIG. 10, where first HR value 1052 was marked by a marking 1054.

At another operation 1590, at least some of the first HR values are stored, for example in the memory of device 1400, or in memory 1443. In embodiments, the thus stored HR values have been thus derived from the stored WCD system data which, in turn may be generated from at least one hour of the sensed ECG signal, and hopefully the entire duration 1077.

And, at another operation 1595, the stored first HR values may be displayed. Further, error indicia may also be displayed in relation to the displayed first HR values that are marked as error-prone.

Of course, additional embodiments are possible as a long-term rate is ultimately constructed from short segments. For example, in embodiments, it is further possible to aggregating groups of the first time bins 540, 1040 into respective second time bins 570. It is also possible to derive second HR values 580 for respective ones of the second time bins, from at least some of the first HR values of the first time bins that are aggregated into the certain second time bin. This can be by the middlemost-ranked values, by averaging, etc. In such cases, the second HR values can be stored instead of the first HR values, and so on. And again, errors such as outliers within the second time bins may be discarded, for example by techniques similar to what was described above.

Moreover, at least some of the second HR values can be marked as error-prone, if derived for second time bins that include aggregated first time bins from which raw HR values were discarded. Then the stored second HR values can be displayed, along with error indicia in relation to the displayed second HR values that are marked as error-prone.

In some embodiments, if there are too many errors, nothing is displayed, for example as seen in FIG. 13. This is because, in embodiments it is preferable to omit data than to show data for which there is little confidence. Below is a discussion as to what constitutes too many errors, for purposes of the invention.

Indeed, at the recommended values, there are 24 raw HR values every minute. Of those, up to 23 noisy ones can be discarded and one would still have a meaningful value for that minute, for purposes of the invention. If some, or most, of the raw HR values for one minute are discarded, there isn't really much consequence to the user who is looking for a long-term trend. One probably does not need to do anything special to show that many data has been discarded at the minute level.

On a larger scale, there are 60 minutes in an hour. Of those, up to 59 bad ones can be discarded, and would still leave a data point to plot for that hour, but that becomes incrementally less meaningful for purposes of the invention. And, the fewer the data points, the less meaningful the maximum and the minimum values become, even though, technically speaking, they would not be incorrect.

Figure 16:
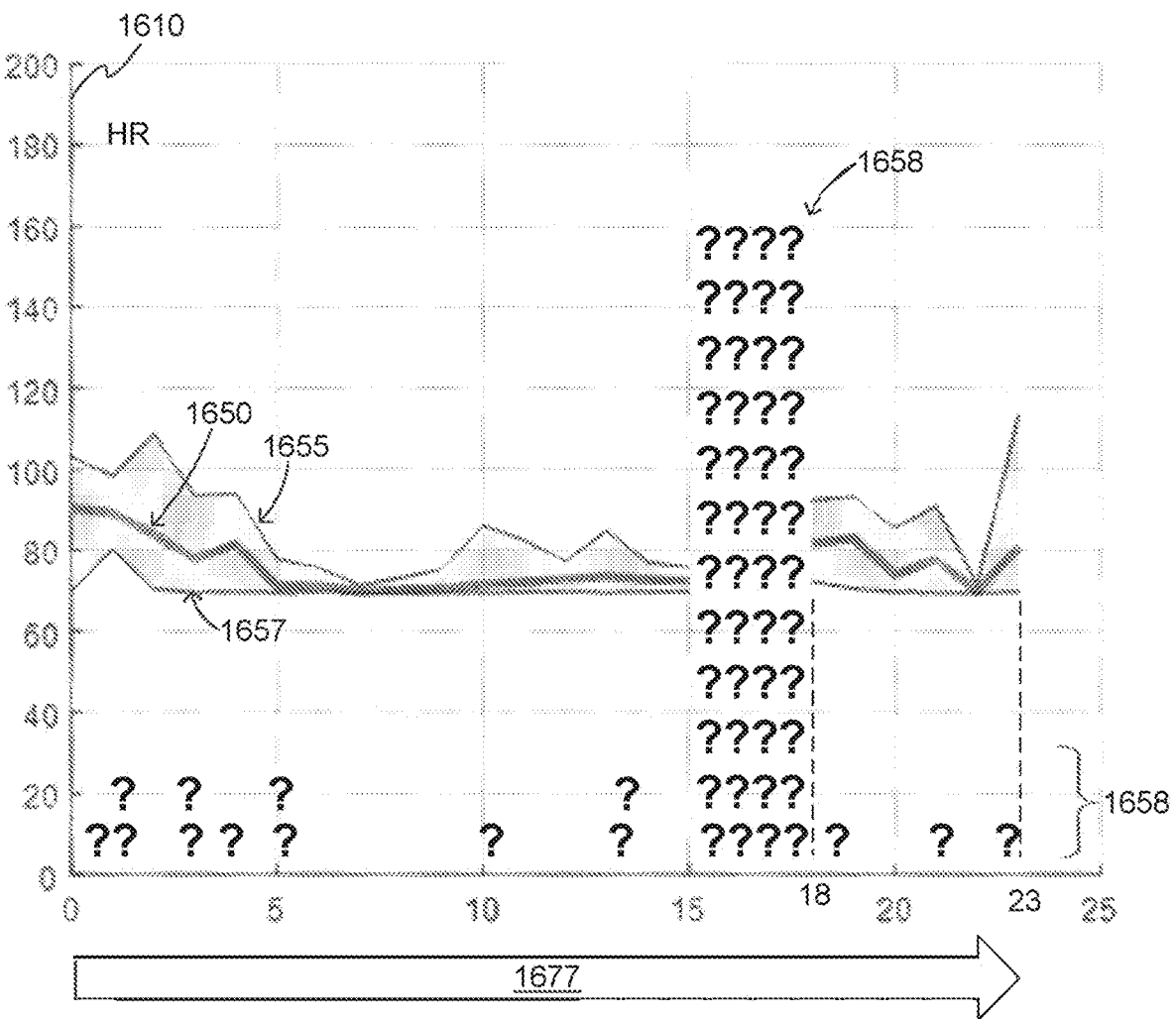
FIG. 16 is a diagram of a sample displayed long-term heart rate of a patient, according to yet other embodiments.

Referring now to FIG. 16, a vertical axis 1610 indicates final heart rate values, which can be the first heart rate values, second heart rate values, and so on. A time duration 1677 is parallel to a horizontal axis that is demarcated in hours.

A diagram of a sample displayed long-term heart rate of a patient is indicated by a line 1650. In this example, additionally a maximum 1655 and a minimum 1657 lines are also shown.

In this embodiment, error indicia 1658 are also displayed. In this example, error indicia 1658 are displayed as question marks associated with the hour involved, by being arrayed first along the hour involved. In addition, their height starts from the horizontal time axis and small HR values where it would be unobtrusive to the reading, and from there it goes up commensurately with the amount of doubt that should accompany their readings of that hour. And, where a threshold of error values is exceeded, the error indicia 1658 overtakes the ordinary and expected values of a HR trend, such as between hours 15-18. Indeed, for those 3 hours, no HR trend is indicated because the readings are too error-prone. In this example, this overtaking is shown as a continuum, but other examples are also possible.

In the methods described above, each operation can be performed as an affirmative act or operation of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A computer system for helping monitor a patient, the patient having worn a wearable medical monitor (WMM) system for at least one hour during which the WMM system included a plurality of Electrocardiogram (ECG) electrodes, a discharge circuit to store electrical charge, a support structure worn by the patient so as to maintain the plurality of ECG electrodes on a body of the patient, the plurality of ECG electrodes thus defining two or more channels and sensing two or more versions of an ECG signal of the patient across the two or more channels, a WMM processor analyzing short segments of the sensed ECG signal, and a memory storing WMM system data about the sensed ECG signal, the stored WMM system data being generated from the at least one hour of the sensed ECG signal, the computer system comprising:

one or more computer processors distinct from the WMM processor; and a non-transitory computer-readable storage medium storing instructions which, when executed by the one or more computer processors, result in operations comprising:

receiving the stored WMM system data;

inputting computed raw heart rate (HR) values for respective ones of the short ECG signal segments;

aggregating groups of the computed raw HR values into respective first time bins that are arranged in a time sequence;

discarding, from their respective first time bins, computed raw HR values that meet an error condition, wherein a computed raw HR value in a certain one of the first time bins meets the error condition when the computed raw HR value differs from another raw HR value aggregated into the certain one of the first time bins by at least an error HR threshold, and no two other raw HR values aggregated into the certain one of the first time bins differ from each other by as much as the error HR threshold;

deriving first HR values for respective ones of the first time bins, a first HR value of a certain one of the first time bins being derived from the computed raw HR values aggregated and remaining into the certain one of the first time bins after the computed raw HR values that meet the error condition are discarded, wherein the first HR value is derived using a median-based selection of the remaining HR values;

storing at least some of the first HR values, the stored first HR values having been thus derived from the stored WMM system data that is generated from the at least one hour of the sensed ECG signal; and utilizing the stored first HR values to perform long-term monitoring of heart rate of the patient, wherein the long-term monitoring of the heart rate of the patient comprises detecting a medical condition of the patient, and wherein the medical condition comprises a shockable arrhythmia;

wherein responsive to detecting the medical condition and determining that a shock criterion is met, the WMM system is configured to cause at least some of the electrical charge stored in the discharge circuit to be discharged through the patient while the support structure is worn by the patient, to deliver a shock to the patient.

2. The computer system of claim 1, wherein:

the stored WMM system data encodes amplitude values of the sensed ECG signal, and when the instructions are executed by the one or more computer processors, the resulting operations further comprise:

computing, from the amplitude values, the raw HR values that are subsequently inputted.

3. The computer system of claim 1, wherein:

the WMM processor further computes the raw HR values, and the stored WMM system data includes the raw HR values that are subsequently inputted.

4. The computer system of claim 1, wherein the error condition includes that one of the plurality of ECG electrodes is detected to be off.

5. The computer system of claim 1, wherein the error condition includes that, in at least one of the two or more versions, a detected noise exceeds a noise threshold.

6. The computer system of claim 1, wherein:

when the instructions are executed by the one or more computer processors, the resulting operations further comprise:

after deriving and before storing, replacing a certain one of the first HR values of a certain one of the first time bins by an adjusted first HR value that is derived from the first HR value of the first time bin that is within a filter range of the certain one of the first time bins in the time sequence, and is not derived from the certain one of the first HR values.

7. The computer system of claim 1, further comprising:

a screen, and wherein when the instructions are executed by the one or more computer processors, the resulting operations further comprise:

marking as error-prone at least some of the first HR values derived for the first time bins from which the computed raw HR values were discarded; and displaying the stored first HR values, and displaying error indicia in relation to the displayed first HR values that are marked as error-prone.

8. The computer system of claim 1, wherein:

when the instructions are executed by the one or more computer processors, the resulting operations further comprise:

aggregating groups of the first time bins into respective second time bins; and deriving second HR values for respective ones of the second time bins, the second HR value of a certain one of the second time bins being derived from at least some of the first HR values of the first time bins that are aggregated into the certain one of the second time bins, and the second HR values are stored instead of the first HR values.

9. The computer system of claim 8, further comprising:

a screen, and wherein when the instructions are executed by the one or more computer processors, the resulting operations further comprise:

marking as error-prone at least some of the second HR values derived for second time bins that include aggregated first time bins from which the computed raw HR values were discarded;

displaying the stored second HR values; and displaying error indicia in relation to the displayed second HR values that are marked as error-prone.

10. A method for helping monitor a patient, the patient having worn a wearable medical monitor (WMM) system for at least one hour during which the WMM system included a plurality of Electrocardiogram (ECG) electrodes, a discharge circuit to store electrical charge, a support structure worn by the patient so as to maintain the plurality of ECG electrodes on a body of the patient, the plurality of ECG electrodes thus defining two or more channels and sensing two or more versions of an ECG signal of the patient across the two or more channels, a WMM processor analyzing short segments of the sensed ECG signal, and a memory storing WMM system data about the sensed ECG signal, the stored WMM system data being generated from the at least one hour of the sensed ECG signal, the method being performed by one or more computer processors distinct from the WMM processor, and the method comprising:

receiving the stored WMM system data;

inputting computed raw heart rate (HR) values for respective ones of the short ECG signal segments;

aggregating groups of the computed raw HR values into respective first time bins that are arranged in a time sequence;

discarding, from their respective first time bins, the computed raw HR values that meet an error condition, wherein a computed raw HR value in a certain one of the first time bins meets the error condition when the computed raw HR value differs from another raw HR value aggregated into the certain one of the first time bins by at least an error HR threshold, and no two other raw HR values aggregated into the certain one of the first time bins differ from each other by as much as the error HR threshold;

deriving first HR values for respective ones of the first time bins, a first HR value of a certain one of the first time bins being derived from the computed raw HR values aggregated and remaining into the certain one of the first time bins after the computed raw HR values that meet the error condition are discarded, wherein the first HR value is derived using a median-based selection of the remaining HR values;

storing at least some of the first HR values, the stored first HR values having been thus derived from the stored WMM system data that is generated from the at least one hour of the sensed ECG signal; and utilizing the stored first HR values to perform long-term monitoring of heart rate of the patient, wherein the long-term monitoring of the heart rate of the patient comprises detecting a medical condition of the patient, and wherein the medical condition comprises a shockable arrhythmia;

wherein responsive to detecting the medical condition and determining that a shock criterion is met, the WMM system is configured to cause at least some of the electrical charge stored in the discharge circuit to be discharged through the patient while the support structure is worn by the patient, to deliver a shock to the patient.

11. The method of claim 10, wherein the stored WMM system data encodes amplitude values of the sensed ECG signal, and the method further comprising:

computing, from the amplitude values, the raw HR values that are subsequently inputted.

12. The method of claim 10, wherein:

the WMM processor further computes the raw HR values, and the stored WMM system data includes the raw HR values that are subsequently inputted.

13. The method of claim 10, wherein the error condition includes that one of the plurality of ECG electrodes is detected to be off.

14. The method of claim 10, wherein the error condition includes that, in at least one of the two or more versions, a detected noise exceeds a noise threshold.

15. The method of claim 10, further comprising:

after deriving and before storing, replacing a certain one of the first HR values of a certain one of the first time bins by an adjusted first HR value that is derived from the first HR value of the first time bin that is within a filter range of the certain one of the first time bins in the time sequence, and is not derived from the certain one of the first HR values.

16. The method of claim 10, further comprising:

marking as error-prone at least some of the first HR values derived for first time bins from which the computed raw HR values were discarded; and displaying the stored first HR values, and displaying error indicia in relation to the displayed first HR values that are marked as error-prone.

17. The method of claim 10, further comprising:

aggregating groups of the first time bins into respective second time bins; and deriving second HR values for respective ones of the second time bins, the second HR value of a certain one of the second time bins being derived from at least some of the first HR values of the first time bins that are aggregated into the certain one of the second time bins, and the second HR values are stored instead of the first HR values.

18. The method of claim 17, further comprising:

marking as error-prone at least some of the second HR values derived for second time bins that include aggregated first time bins from which the computed raw HR values were discarded;

displaying the stored second HR values; and displaying error indicia in relation to the displayed second HR values that are marked as error-prone.

* * * * *